United States Patent
Friedman

(10) Patent No.: US 9,726,768 B2
(45) Date of Patent: Aug. 8, 2017

(54) PLASMA PANEL BASED IONIZING-PARTICLE RADIATION DETECTOR

(71) Applicant: Integrated Sensors, LLC, Toledo, OH (US)

(72) Inventor: Peter S. Friedman, Toledo, OH (US)

(73) Assignee: INTEGRATED SENSORS, LLC, Toledo, OH (US)

(*) Notice: Subject to any disclaimer, the term of this patent is extended or adjusted under 35 U.S.C. 154(b) by 0 days.

(21) Appl. No.: 13/626,053

(22) Filed: Sep. 25, 2012

(65) Prior Publication Data
US 2013/0068956 A1  Mar. 21, 2013

Related U.S. Application Data

(63) Continuation of application No. 12/763,807, filed on Apr. 20, 2010, now abandoned.
(Continued)

(51) Int. Cl.
  *G08B 17/12* (2006.01)
  *G01T 1/26* (2006.01)
  (Continued)

(52) U.S. Cl.
  CPC .............. *G01T 1/26* (2013.01); *A61N 5/1075* (2013.01); *G01T 1/2935* (2013.01); *H01J 47/08* (2013.01);
  (Continued)

(58) Field of Classification Search
  CPC .......... A61B 6/4258; A61N 2005/1087; A61N 5/1075; G01T 1/26; G01T 1/2935;
  (Continued)

(56) References Cited

U.S. PATENT DOCUMENTS 5,159,231 A * 10/1992 Feller ................ H01J 43/246
                                                250/207
5,471,112 A * 11/1995 Hamon ................ H01J 11/10
                                                313/485
(Continued)

OTHER PUBLICATIONS

Peter S. Friedman; "Plasma Panel Sensors as Scintillation Detectors"; Nuclear Science Symposium Conference Record, 2006; IEEE, Piscataway, NJ, USA; Oct. 1, 2006, pp. 1150-1159; XP031083569; ISBN: 978-1-4244-0560-2.
(Continued)

*Primary Examiner* — Naomi Small
(74) *Attorney, Agent, or Firm* — Miles & Stockbridge P.C.

(57) ABSTRACT

A position-sensitive ionizing-particle radiation counting detector includes a first substrate and a second substrate generally parallel to the first substrate and forming a gap with the first substrate, with a discharge gas contained within the gap. The detector includes a first electrode electrically coupled to the second substrate, and a second electrode electrically coupled to the first electrode and defining at least one pixel with the first electrode. The detector further includes an open dielectric structure pattern layered over one of the first or second electrodes and a current-limiting quench resistor coupled in series to one of the first or second electrodes. The detector further includes a power supply coupled to one of the first or second electrodes and a first discharge event detector circuitry coupled to the one of the first or second electrodes for detecting a gas discharge counting event in the electrode.

28 Claims, 16 Drawing Sheets

Related U.S. Application Data

(60) Provisional application No. 61/214,149, filed on Apr. 20, 2009.

(51) Int. Cl.
| | |
|---|---|
| *H01L 31/115* | (2006.01) |
| *G01T 1/29* | (2006.01) |
| *H01J 47/08* | (2006.01) |
| *A61N 5/10* | (2006.01) |
| *A61B 6/00* | (2006.01) |

(52) U.S. Cl.
CPC .......... *H01L 31/115* (2013.01); *A61B 6/4258* (2013.01); *A61N 2005/1087* (2013.01)

(58) Field of Classification Search
CPC .. H01J 47/08; H01J 11/12; H01J 11/36; H01J 11/38; H01J 17/485; H01L 31/115
USPC .......................................................... 340/600
See application file for complete search history.

(56) References Cited

U.S. PATENT DOCUMENTS

| | | | | |
|---|---|---|---|---|
| 5,572,135 | A * | 11/1996 | Owens ................... | F02P 17/12 324/380 |
| 5,731,584 | A | 3/1998 | Beyne et al. | |
| 5,747,169 | A * | 5/1998 | Fan ...................... | B01J 19/0093 428/426 |
| 6,051,928 | A * | 4/2000 | Choi ....................... | H01J 11/38 313/582 |
| 6,317,248 | B1 * | 11/2001 | Agrawal ................. | G02F 1/155 340/438 |
| 6,777,681 | B1 * | 8/2004 | Schimert .................. | G01J 5/20 250/330 |
| 6,822,239 | B2 | 11/2004 | Tanimori et al. | |
| 7,230,751 | B2 * | 6/2007 | Whitesides ............. | G02F 1/167 345/107 |
| 2003/0227253 | A1* | 12/2003 | Seo ..................... | H01L 27/3246 313/504 |
| 2005/0001201 | A1* | 1/2005 | Bocko ...................... | B32B 7/06 252/299.01 |
| 2006/0049362 | A1* | 3/2006 | Friedman ................ | C22C 19/05 250/374 |
| 2006/0071595 | A1* | 4/2006 | Woo ....................... | H01J 11/12 313/584 |
| 2009/0168357 | A1* | 7/2009 | Suzuki .................... | H05K 5/02 361/709 |
| 2010/0014631 | A1* | 1/2010 | Sonsky ................. | G01T 1/2018 378/19 |

OTHER PUBLICATIONS

Peter S. Friedman; "A New Class of Low Cost, High Performance Radiation Detectors"; Nuclear Science Symposium conference Record, 2005 IEEE Wyndham El conquistator Resort, Puerto Rico, Oct. 23-29, 2005; Pescataway, NJ, USA; IEEE, vol. 5, Oct. 23, 2005; pp. 2815-2822; XP010896250; ISBN: 978-0-7803-9221-2.

* cited by examiner

PLASMA PANEL BASED IONIZING-PARTICLE RADIATION DETECTOR

RELATED APPLICATIONS

This application is a continuation of U.S. patent application Ser. No. 12/763,807, filed on Apr. 20, 2012, which claims priority to U.S. Provisional Patent Application No. 61/214,149, filed on Apr. 20, 2009, the specifications of which are herein incorporated by reference.

FIELD

One embodiment of the present invention is directed to the detection and imaging of ionizing-particle radiation. More particularly, one embodiment of the present invention is directed to a plasma panel based apparatus for the detection and imaging of ionizing-particle radiation.

BACKGROUND INFORMATION

Many useful applications, such as the detection of radioactive material and computer-assisted tomography ("CAT"), rely on the detection of photon radiation, known as X-ray and/or gamma-ray radiation. Both of these types of high-energy photon radiation cause ionization and for the purposes of this disclosure the two terms, X-ray and gamma-ray, are used interchangeably. In terms of the detection of such ionizing radiation, the spectral region of greatest interest for most of these applications generally falls between the energies of about 20 keV to 20 MeV. Other applications, including the detection of particle radiation from ion beam accelerators/colliders, cosmic ray generated minimum ionizing particles (MIP's), and neutrons from special nuclear materials (SNM) used in nuclear weapons (e.g., plutonium), rely on the detection of ionizing particles that can be either atomic (e.g., radioactive ion beams) or subatomic (e.g., neutrons, protons and muons) in nature, and which can vary over a very broad energy range from less than 1 MeV to well beyond 1 TeV.

In order to detect ionizing radiation in the above spectral range of interest, a number of known sensing devices are commonly used. One of the earliest known electronic devices is the ionization chamber. Detection of radiation in an ionization chamber, such as a Geiger-Mueller ("GM") tube, is based upon electrical conductivity induced in an inert gas (usually containing argon and neon) as a consequence of ion-pair formation. One currently widely used type of ionizing-particle radiation detector is the micropattern gas detector. These devices have been under continuous development for many years in high energy and nuclear physics. Detectors such as the Microstrip Gas Chamber ("MSGC"), Gas Electron Multiplier ("GEM") and Micromegas have many desirable properties as proportional gas detectors, but are operationally limited to gains within the proportional region in the range of $\sim 10^3$ to $10^6$.

SUMMARY

One embodiment is a plasma panel based ionizing-particle radiation detector that includes a first substrate and a second substrate coupled to the first substrate by a hermetic seal. The second substrate is an ultra-thin substrate. The detector further includes a discharge gas between the first and second substrate and at least one second electrode electrically coupled to a first electrode and defining at least one pixel with the first electrode. The second electrode is coupled to the first substrate and a first impedance is coupled to the first electrode. The detector further includes a power supply coupled to at least the first or second electrode and a first discharge event detector circuitry is coupled to at least one of the first or second electrodes for detecting a gas discharge counting event in the electrode. The detector further includes a plurality of pixels, each pixel capable of outputting a gas discharge pulse upon interaction with ionizing-radiation. Each gas discharge pulse is counted by the detector as having approximately an equal value and circuitry detects if a gas discharge pulse is output from the pixels, and counts each gas discharge pulse as an individual event.

DETAILED DESCRIPTION

Figure 1:
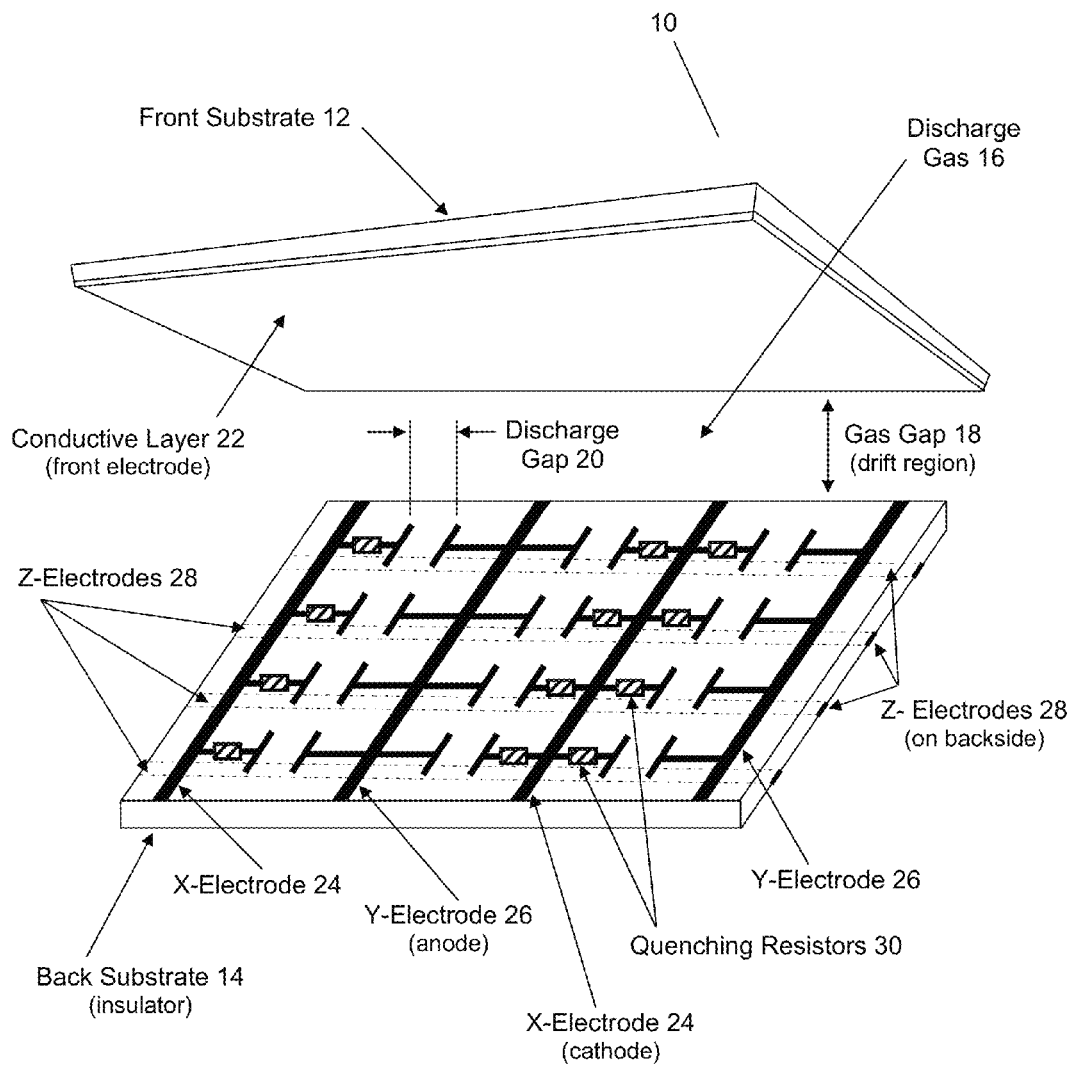
FIG. 1 is a perspective view of a surface-discharge plasma panel sensor ("PPS") and/or plasma panel photosensor ("PPPS") detector with a parallel/rectilinear surface-discharge electrode pattern incorporating individual cell quenching resistors and an orthogonal back electrode pattern in accordance with one embodiment of the present invention.

One embodiment is a plasma panel sensor ("PPS") device that provides enhanced detection, tracking, identification and imaging of ionizing particles generated in nuclear accelerators and particle colliders, as well as the detection of such particles occurring naturally or created by other means. The particles to be detected are numerous and can encompass new classes of ionizing particles as yet to be discovered. Embodiments used with accelerator/colliders provide detection, monitoring and profiling of protons and heavier ions such as carbon and neon ions in the treatment of cancer by hadron particle beam therapy, the detection, monitoring, tracking and profiling of very large ionizing particles generated in radioactive ion beam ("RIB") accelerators, the detection and tracking of subatomic ionizing particles such as muons generated in facilities such as the Large Hadron Collider ("LHC") at CERN, and the use of such particles for materials characterization, testing and non-destructive testing at facilities such as the Spallation Neutron Source ("SNS") at Oak Ridge National Laboratory.

A plasma display panel ("PDP") based sensor, or "plasma panel sensor" (PPS") and light-sensitive plasma panel photosensor ("PPPS") used for radiation detection has been disclosed, for example, in U.S. Pat. Nos. 7,332,726 and 7,564,039 and 7,683,340, and utilizes some of the structure and manufacturing techniques used in producing plasma display panels for television. These devices can be considered hybrid gaseous solid state sensors that encompass some of the best features of Geiger-Mueller ("GM") tubes and micropattern gas detectors. However, they can provide a much greater sensitivity than micropattern detectors, operating beyond the proportional region and in what is generally called the Geiger-Mueller region with internal gains on the order of ~$10^6$ or higher (depending upon pixel resolution, etc.), with position resolutions that can approach 10 μm, a temporal resolution estimated at about 100 ps or better, and insensitivity to magnetic fields. Unlike conventional micropattern detectors, PPS's are inherently digital devices and can greatly expand the capability of micropattern detection technology for both charged and neutral species over the full range from minimum to maximum ionizing particles (e.g., muons to radioactive ion beams).

Fabrication of the PPS can utilize low cost photolithographic techniques for construction of the electrodes, and a gaseous media for electron amplification. Further, fabrication can take advantage of a huge multi-billion dollar technology base developed over a 40 year period for the manufacturing and materials infrastructure of PDP modules. Such PDP's are mass-produced as large area (e.g., 1-2 meter diagonal), flat panel HDTV-sets and currently sell with electronics for less than $0.30 per square inch, which is about two orders-of-magnitude less expensive than the lowest cost photomultiplier tubes ("PMT"s). PPS-based detectors address many of the properties sought in the next-generation of position-sensitive, minimum and maximum ionizing-particle detectors (e.g., for muons, pions, kaons, fast electrons, protons, etc.) for high energy and nuclear physics, to provide significant position, tracking and timing resolution improvement, radiation hardness, high sensitivity and enhanced rate capability, improved stability, compactness and low cost. In addition, the combination of high pixelation with ultra-fast response time allows the PPS to serve simultaneously as both a fast triggering device and a high resolution positional detector for both low and high luminosity sources.

The PDP was invented in the early 1960's as a flat panel display to replace the cathode ray tube ("CRT"). The PDP is the device that makes the plasma-television ("TV") possible. It is composed of millions of cells per square meter, each of which typically can initiate and sustain a plasma discharge for at least a few hundred nanoseconds. The cells are quite small, generally about 100 to 200 μm in each dimension for both the pitch and gas gap in a 1 meter diagonal display. Because of their small size, large electric fields are easily produced with only a few hundred volts of bias. The plasma discharges, which are well-controlled and confined, employ various Xe gas mixtures (e.g., ~5% Xe in 95% Ne) at less than an atmosphere of pressure (e.g., 500-600 torr). In the PDP, the discharge produces both ultraviolet ("UV") and vacuum-ultraviolet ("VUV") light that strikes phosphors in the cells and produces the bright colors characteristic of plasma TV's (each pixel typically contains a red, green and blue cell). At any given time in a TV picture, many of the pixels have at least one cell on, so the PDP electronics must individually address, refresh and sustain these discharges, while quickly suppressing cells that must change state by "erasing" their stored charge on the surface dielectric.

In a PDP configured for radiation detection, each cell can be biased to discharge when a free-electron is generated in, or emitted into, the gas. The PPS, as a reconfigured PDP, thus functions as a highly integrated array of parallel pixel-sensor-elements or cells, each independently capable of detecting free-electrons within the cell that are due to incident ionizing-particle radiation (since all PPS devices are "monochrome", the terms "pixel" and "cell" are synonymous for these devices). For example, free-electrons and ions generated by interaction of the gas with a minimum ionizing particle ("MIP") (e.g., a muon) passing through the PPS cell can in turn lead to rapid electron multiplication resulting in an avalanche that can be confined to the local pixel cell space. For known plasma panel based devices, this avalanche process is self-limiting and self-contained. The discharge current of an individual triggered cell is unimportant, only the fact that a cell is either "ON" or "OFF" (i.e., pixel switching). The PPS is therefore intrinsically digital, and, with a gain of ~$10^6$ is large enough that for many applications it can potentially avoid having to use external signal amplification electronics, especially considering that the PPS is a digital, particle-counting device and thus achieves its sensitivity because it can operate in the Geiger region, as compared to the proportional region for most known detectors which are proportional detectors. Thus, PPS-based detectors, including light-sensitive PPS-based detectors (i.e., the PPPS), can have a much higher gain than proportional detectors.

For a plasma panel operating as a TV monitor in the display mode, the pixel switching is initiated by video signals applied through a network of driver circuits. As a PPS detector the switching can be triggered either by direct ionization of the gas from incident ionizing particles, or indirectly via the incident ionizing radiation interacting with an internal conversion layer within the PPS that emits electrons into the gas. When a pixel/cell is turned "ON" by absorbed or inelastically scattered radiation, a signal can be collected by the readout electronics and an image or tracking point generated. A large number of device structures are possible with a variety of readout options (both electronic and optical), including the columnar structure (with anode and cathode on opposite substrates) and the surface-discharge structure (with anode and cathode on the same substrate), the latter used on virtually all PDP's sold today.

Some key characteristics of the PPS are its high gain, fine positional resolution, fast response, radiation hardness, insensitivity to magnetic fields, and potentially high electron detection efficiency. In terms of device resolution, a pixel pitch of 50 to 100 μm should be more than sufficient for most high luminosity accelerators in preventing signal pileup associated with two independent incident ionizing-particles falling within the same pixel discharge cell space at essentially the same time (i.e., within the cell gas discharge response period). In fact, a pixel pitch of about 200 μm should be more than adequate for many applications in nuclear physics. Regarding fabrication of such devices, 21-inch diagonal AC-PDP's with a cell pitch of 108 μm have been fabricated in the past. The pixel structure of these AC-PDP's was quite complex, significantly more so than for most PPS devices, as these display panels required RGB phosphor patterning and alignment via screen-printing and were fabricated on a high coefficient of thermal expansion (i.e. $90 \times 10^{-7}/° C.$) float glass substrate. In contrast, PPS devices do not require difficult-to-control, thick film, screen-printing and phosphor pattern pixel alignment on "thermally unstable" float glass substrates. PPS devices fabricated on glass can use much more stable, non-alkali, lower expansion substrate materials such as alkaline earth boro-aluminosilicate flat panel display glass (e.g., Corning Eagle-XG) with a thermal expansion of $\sim 32 \times 10^{-7}/° C.$, as compared to $90 \times 10^{-7}/° C.$ for the above 21-inch AC-PDP's. Finally, embodiments of PPS detectors will almost always be operated as DC devices, and therefore will more closely resemble a DC-PDP than an AC-PDP. The electrode resolution in DC-PDPs can therefore be much higher because the electrodes do not have to be coated and fired with a chemically reactive and corrosive thick-film dielectric that tends to undercut and erode the AC-PDP electrode-material line width. For these reasons it is feasible to fabricate embodiments of PPS devices with a pixel pitch approaching 10 μm. Also in terms of high resolution electrodes, LCD's on glass with a 10-30 μm pixel pitch are now being manufactured, so for PPS devices the fabrication process could utilize similar technology. Finally, as a collateral benefit, minimizing the electrode width also raises the intrinsic firing voltage, thereby increasing the pixel electric-field strength and hence the device sensitivity.

For most of the embodiments of the present invention, each plasma panel cell can in some ways be thought of as a miniature GM-tube or micro-Geiger cell, and GM-counters have very long recovery times. However, PPS rise times can be significantly less than a nanosecond (e.g., in the picosecond range), with recovery times many orders-of-magnitude faster than GM-tubes. This large difference in discharge/recovery time is in large part due to geometry, which directly relates to field gradients and space-charge. In both the GM-tube and plasma panel detector, the operating voltage is similar—approximately 400-1000 volts for the plasma panel (depending on cell geometry) and about 500-1500 volts for GM-tubes. However, the anode to cathode gap in a GM-tube is typically about 10-20 mm, whereas in a plasma panel it is on the order of 0.10-0.20 mm, a reduction of two orders-of-magnitude. All other things being equal, this translates into a field gradient that is 100× greater for the plasma panel. However, the result is much greater because the cathode "wire" in a plasma panel is a narrow electrode, as is the anode, whereas in a GM-counter the cathode comprises the entire inner surface of the cylindrical tube, which could easily be $10^4$ mm². The difference between the cathode area for a medium size GM-tube, and a plasma panel detector, could thus be four orders-of-magnitude (i.e., $10^4$). It follows that the "slow-moving" ions in a plasma panel can be "cleared-out" very quickly, because they need only travel tens of microns to the cathode and are being pulled by a very strong electric field. Contrast this to the GM-tube, where the cathode field strength is many orders-of-magnitude smaller than for the plasma panel, and where the ions have a much longer distance to travel to reach the cathode—perhaps 10 mm. Because of the very weak field in the vicinity of the GM-cathode, the ion movement towards the cathode is almost a random-walk compared to the movement of ions near the plasma panel cathode. Thus for all gas discharge devices (e.g., GM-tubes and plasma panels) the rise time primarily reflects the electron efficiency in going from the cathode region to the anode, whereas the fall time primarily reflects clearing-out the space-charge volume of slow moving ions from the drift region typically located much further away. Therefore, the geometric differences in the discharge volume and field gradients for the plasma panel versus GM-tube results in orders-of-magnitude difference in pixel response time. For example, the GM-tube which functionally acts as a single pixel, has a typical discharge volume of $10^{-1}$ to $10^{-2}$ liters, whereas the PPS pixel discharge volume is in the range of $10^{-9}$ to $10^{-12}$ liters.

AC-PDP's have been successfully operated at 1 MHz refresh rates, corresponding to a pixel "ON/OFF" time of 1 μs (e.g., 2% Xe/98% Ne gas mixture and 325 μm pixel pitch). In order for the entire panel to continuously recycle at 1 μs, individual pixel discharge and recovery should be at least an order of magnitude faster (i.e., ~100 ns), with pixel rise times typically being about two orders-of-magnitude faster than the fall time, or ~1 ns. Free-electrons in a gas discharge, owing to their low mass and small cross-section, achieve a much greater acceleration between encounters with surrounding neutral gas species than ionized atoms, with the result that their mobility can be 1000 times greater than that of ions. In addition, as the percent Xe increases from 2% in the above AC-PDP to perhaps 90-100% in a PPS, so does the gas discharge response speed. Also, as the pixel pitch gets smaller, the discharge gap decreases, raising the field gradient and further reducing the rise time. For embodiments of the PPS, a pixel pitch of 50 to 100 μm is readily achievable. Given all of the above factors, the PPS gas discharge rise time should be shortened by about two to three orders-of-magnitude (i.e., from about 1 ns to approximately 1-10 ps).

Another approximation of response time for a PPS in accordance with one embodiment can be obtained from the pixel RC-time constant. For example, from full panel measurements, a DC-PDP with a pixel pitch of 640 µm may have an isolated pixel capacitance of 30 fF. By comparison, a PPS with a 64 µm pixel pitch would have an isolated pixel capacitance of about 1% of this value, or two orders-of-magnitude smaller (i.e., approximately 0.3 fF). By using a current-limiting, in-line resistor of about 100 kΩ, the shortest time ($\tau$) required to discharge the capacitance would be the RC-time constant, or about 30 ps ($\tau$=RC=100 kΩ×0.3 fF). However, since the rise time is at least an order-of-magnitude faster than the RC discharge time, the corresponding device rise time would be about 3 ps (or faster, especially for a smaller resistor). Thus with a rise time on the order of possibly ~1 ps, the temporal resolution of the embodiments of the PPS could be in the range of about 10 to 100 ps for resolving a discharge tracking event resulting from a single ionizing-particle passing through the PPS drift region.

Given the above value of ~1 ps for the signal rise time, with a fall time perhaps two to three orders-of-magnitude longer, the collection time is approximately on the order of about 0.1 ns to 1 ns. Thus, the PPS particle event total recovery time is in the range of about 1 ns, corresponding to a potential count rate of $10^9$ cps per pixel (i.e., 1 GHz per pixel) or a signal saturation rate limit of $10^{13}$ cps per $cm^2$ for a PPS with a pixel pitch of 100 µm.

Figure 9:
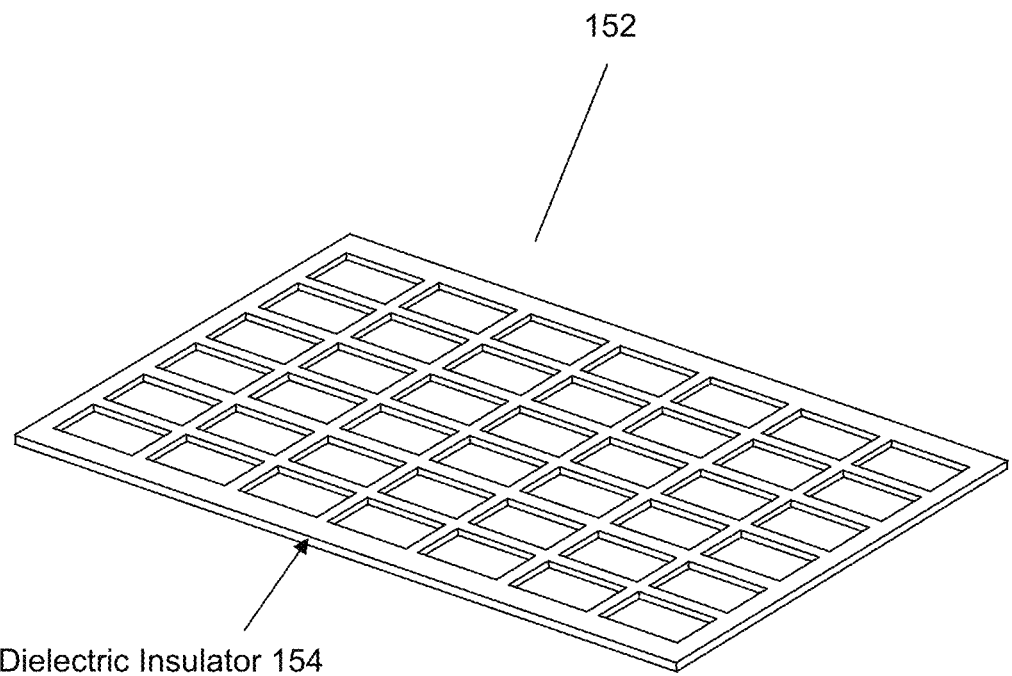
FIG. 9 is a perspective view of a flat dielectric insulator window barrier structure in accordance with one embodiment that can be used with the disclosed detectors.
Figure 10:
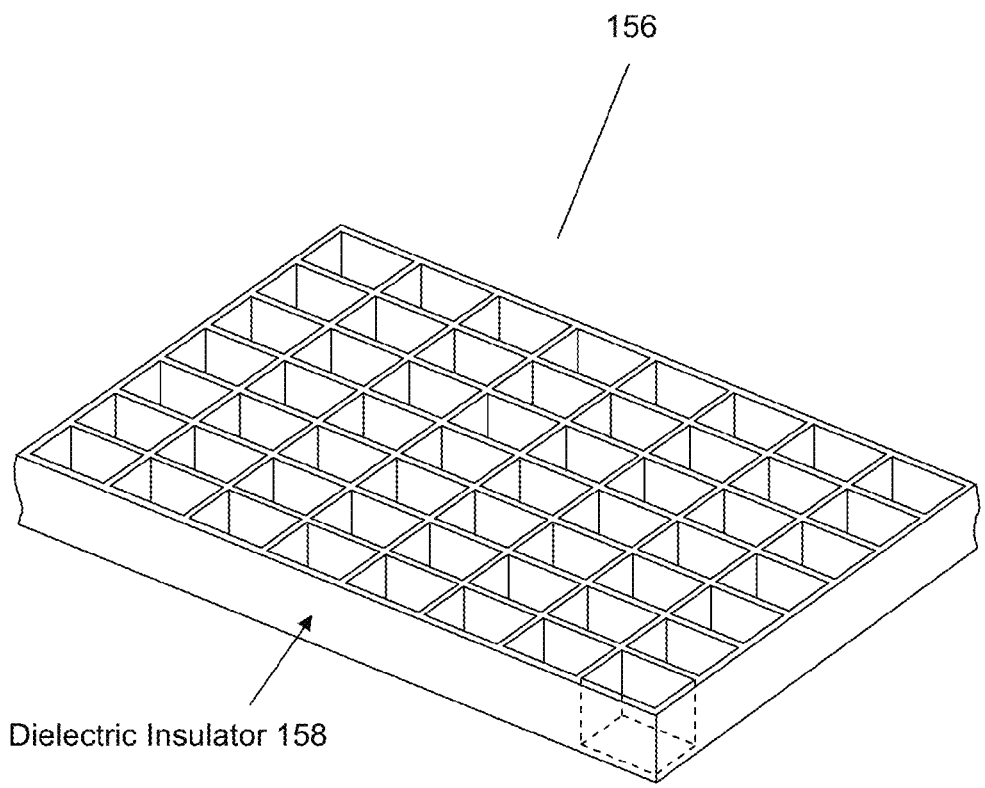
FIG. 10 is a perspective view of a barrier structure in accordance with one embodiment that can be used with the disclosed detectors.

In one embodiment, excited state species (e.g., photons, ions, electrons metastables, etc.) generated in the gas discharge may cause secondary discharges of time-delayed new avalanches. In one embodiment, a quenching agent is added to the gas mixture to "absorb" high energy photons emitted by the gas discharge as well as acting as an energy sink for gas-phase metastables, electrons and ions. In fact, by simply adding a diatomic quenching agent (e.g., oxygen which also served as a Penning gas dopant) to an "open-structure" DC-PDP device, along with the addition of a current limiting series resistor, the problem of secondary avalanches is eliminated with the discharge confined to the nearest pixel interaction site in previously reported PPS devices that were configured as gamma-ray detectors. In another embodiment to prevent gas discharge spreading, each pixel is "enclosed" within a barrier wall structure similar to those used in all commercial PDP-TV's (e.g., as shown in FIG. 10). In another embodiment, to prevent gas discharge spreading, each pixel is surrounded by a "flat" layer of dielectric material similar to that used in commercial DC-PDP's (e.g., as shown in FIG. 9).

In another embodiment, an electrical method can be employed to preventing secondary discharges. In this embodiment quenching resistors are fabricated using low cost thin-film or thick-film technology within each pixel or electrode line that can serve the dual function of both limiting the discharge and decoupling one electrode line or pixel from another.

FIG. 1 is a perspective view of a surface-discharge PPS and/or PPPS detector with a parallel/rectilinear surface-discharge electrode pattern incorporating individual cell quenching resistors and an orthogonal back electrode pattern in accordance with one embodiment of the present invention. PPS 10 includes a first (front) substrate 12 and a second (back) substrate 14, separated by a gas filled gap 18. Sensor 10 includes X-surface discharge electrodes (cathode) 24 and Y-surface discharge electrodes (anode) 26. Detector 10 further includes Z electrodes 28 on the backside of the back substrate 14, quenching resistors 30, and a front conductive layer 22.

PPS 10 is based on surface-discharge, 4-electrode configuration in which the front conductive layer 22 can serve as a front electrode or drift electrode which can also be a thin metal coating. In another embodiment, the front conductive layer can also be a conversion layer or thin sheet such as gadolinium (Gd) foil that can capture an ionizing particle such as a thermal neutron and then emit a fast conversion electron (e.g., 72 keV) into the discharge gas 16. For many applications the PPS front conductive layer 22 can be combined with the front substrate 12 by making the front substrate a metal plate or metal foil. For detector 10, the gas gap is also known as the "drift region".

PPS 10 of FIG. 1 includes a conductive layer as the 4th electrode (i.e., drift electrode or front electrode 22). Detector 10 can be converted to a PPPS by employing for the conductive layer 22 a thin-film photocathode coating. As disclosed above, detector 10 can be converted to a neutron detector by employing for the conductive layer 22 a thin-film Gd neutron conversion layer or Gd neutron conversion foil.

PPS 10 in one embodiment is a highly integrated array with roughly $10^2$ to $10^6$ micro-detection cells per $cm^2$, each of which can act as an independent, position-sensitive, radiation sensor. PPS embodiments, in general, efficiently collect free-electrons and ions created in a gas by the passage of an ionizing particle and then, via the drift field, "channel" the electrons and ions into the higher field region where an avalanche develops.

In each embodiment, the design of the cell can enhance the efficiency. As shown in FIG. 1, in one embodiment of PPS 10, the drift region begins at the front electrode or conversion layer/conductive layer 22 on front substrate 12 (i.e., the cover plate) shown above the avalanche region formed by the X and Y surface-discharge electrodes (i.e., cathode 24 and anode 26). The drift electrode 22 can be either a metallized or transparent conductive coating (e.g., ITO or $SnO_2$) on a dielectric insulating substrate such as glass or ceramic, or the drift electrode can be a metal foil or metal plate. The most effective metals may be the ones with the least photocathodic activity (e.g., metals that are good UV-VUV reflectors with high work functions) which should also be chemically inert with respect to the discharge gas. The selected material should be stable in a plasma discharge environment, so it should have a high melting point and be sputter resistant—two such candidate electrode materials include nickel (Ni) and chromium (Cr).

During operation of PPS 10, interesting tracks are expected to enter the drift region (i.e., gas gap 18 of FIG. 1) somewhat normal to the plane of the drift electrode (i.e., front substrate conductive layer 22). Ions deposited along the track will drift in the uniform part of the field toward the discharge electrodes and enter a large field where an avalanche will begin. Expansion of this avalanche into the high-field region between the cathode (X-electrode 24) and anode (Y-electrode 26) is instrumental to the operation. The avalanche is terminated when the avalanche or discharge voltage drops significantly (e.g., approximately 50% or more in one embodiment) as a result of sufficient resistance in the path that provides high voltage to the X-electrode (i.e., cathode or discharge electrode). The current generated during the avalanche yields the voltage on the Y-electrode (i.e., anode or sense electrode).

In some embodiments, the discharge cathodes protrude vertically into the gas. PPS fabrication technology permits great flexibility in the choice of electrode shapes including elevated wall-like structures with differing cross-sections and heights for the X- and Y-electrodes. Other embodiments utilize planar electrodes having very little height above the substrate surface. Optimization of the electrode shapes are application dependent. PPS electrode configuration embodiments include: those with and without embedded pixel series resistors, with and without orthogonal (Z) strip electrodes beneath the X- and Y-electrodes (see FIG. 1) or on the PPS bottom substrate backside, and the various alternate height vertical electrode structures (disclosed in FIGS. 3-6). High aspect ratio vertical electrodes will allow a larger and more focused drift field to be moved out significantly further into the gas to enhance the detector charged particle collection efficacy.

Figure 3:
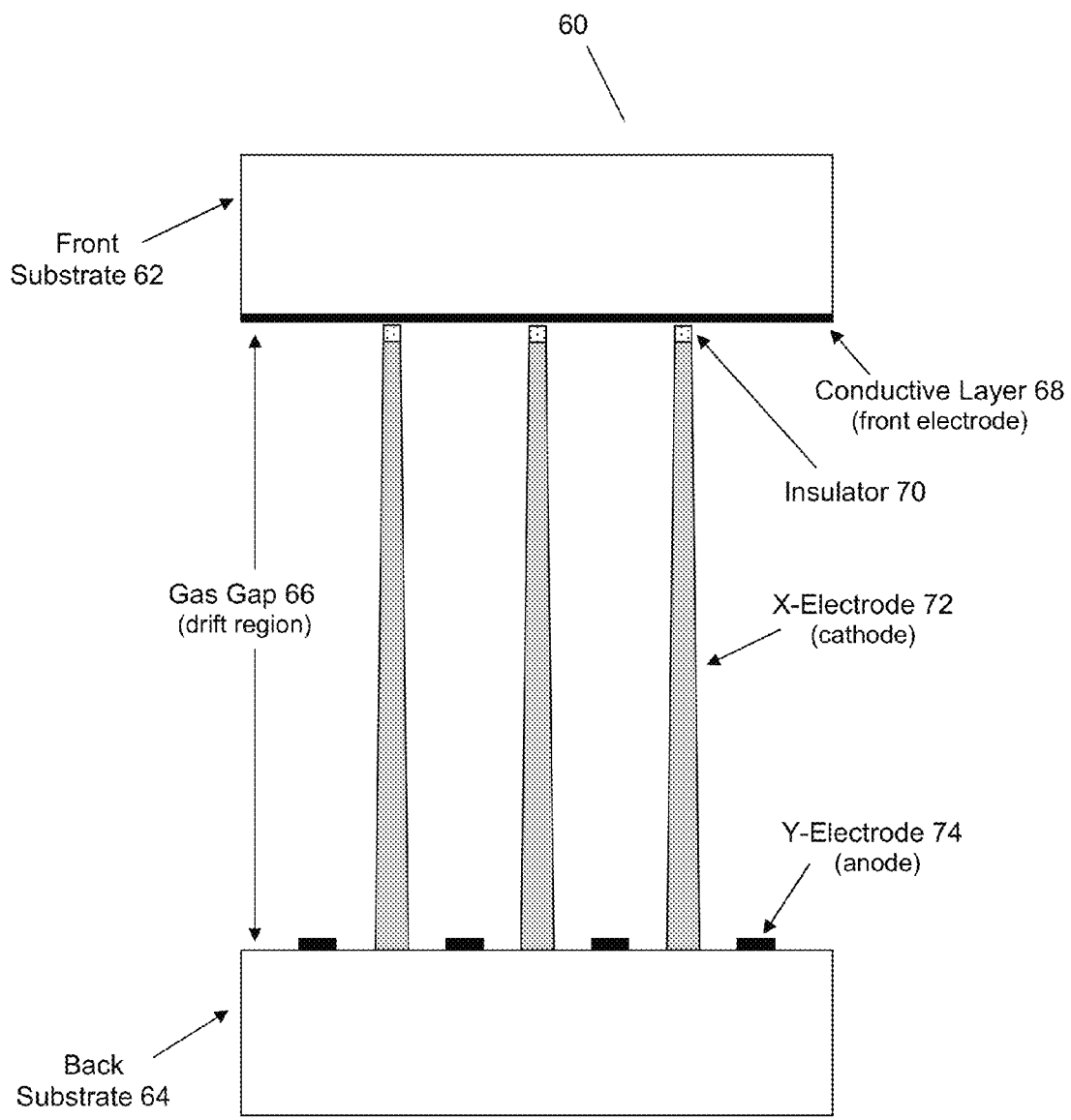
FIG. 3 is a cross-sectional view of a barrier wall vertical electrode structure in accordance with one embodiment that can be used with the disclosed detectors.
Figure 4:
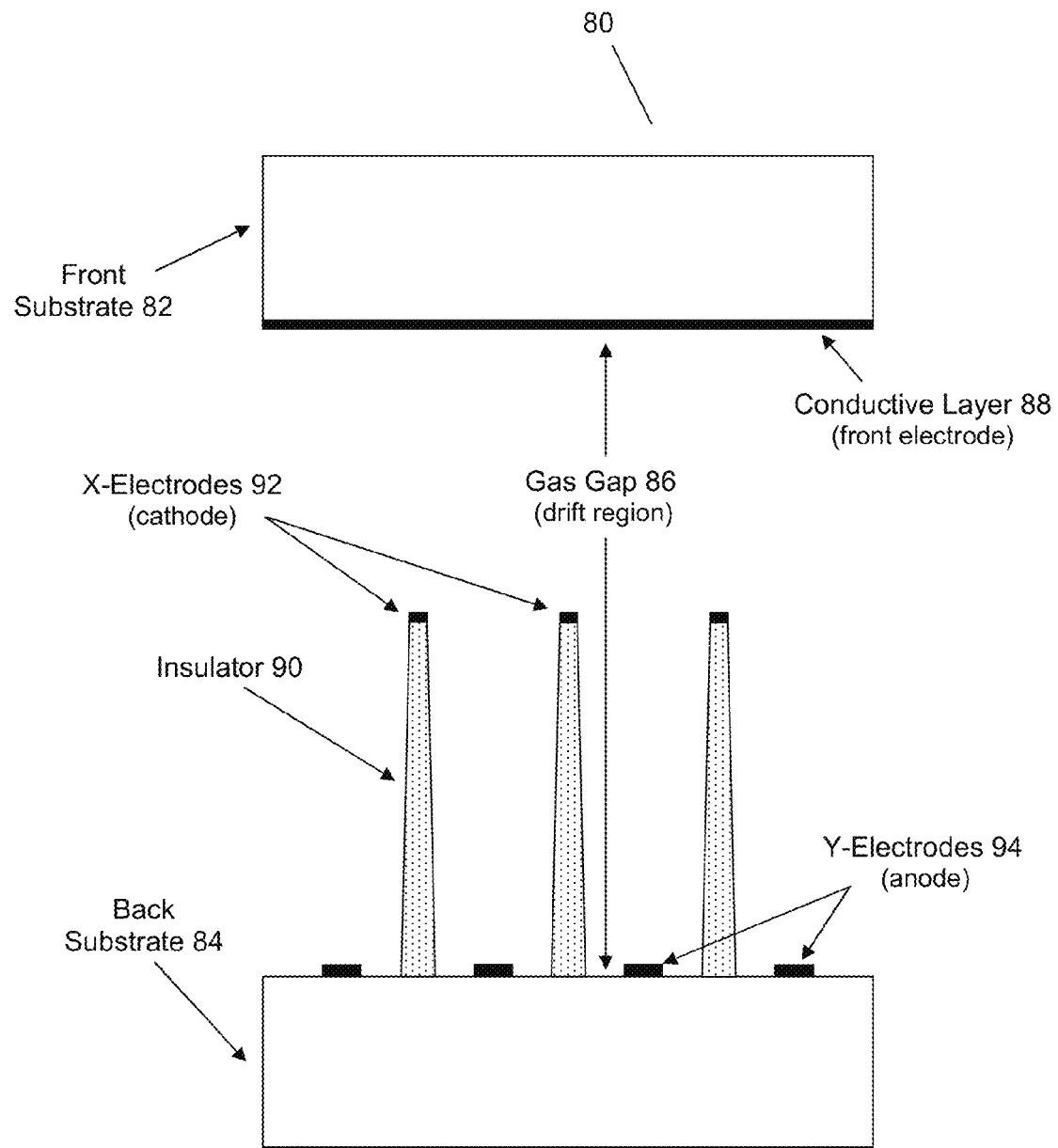
FIG. 4 is a cross-sectional view of an asymmetric elevated vertical electrode structure in accordance with one embodiment that can be used with the disclosed detectors.
Figure 5:
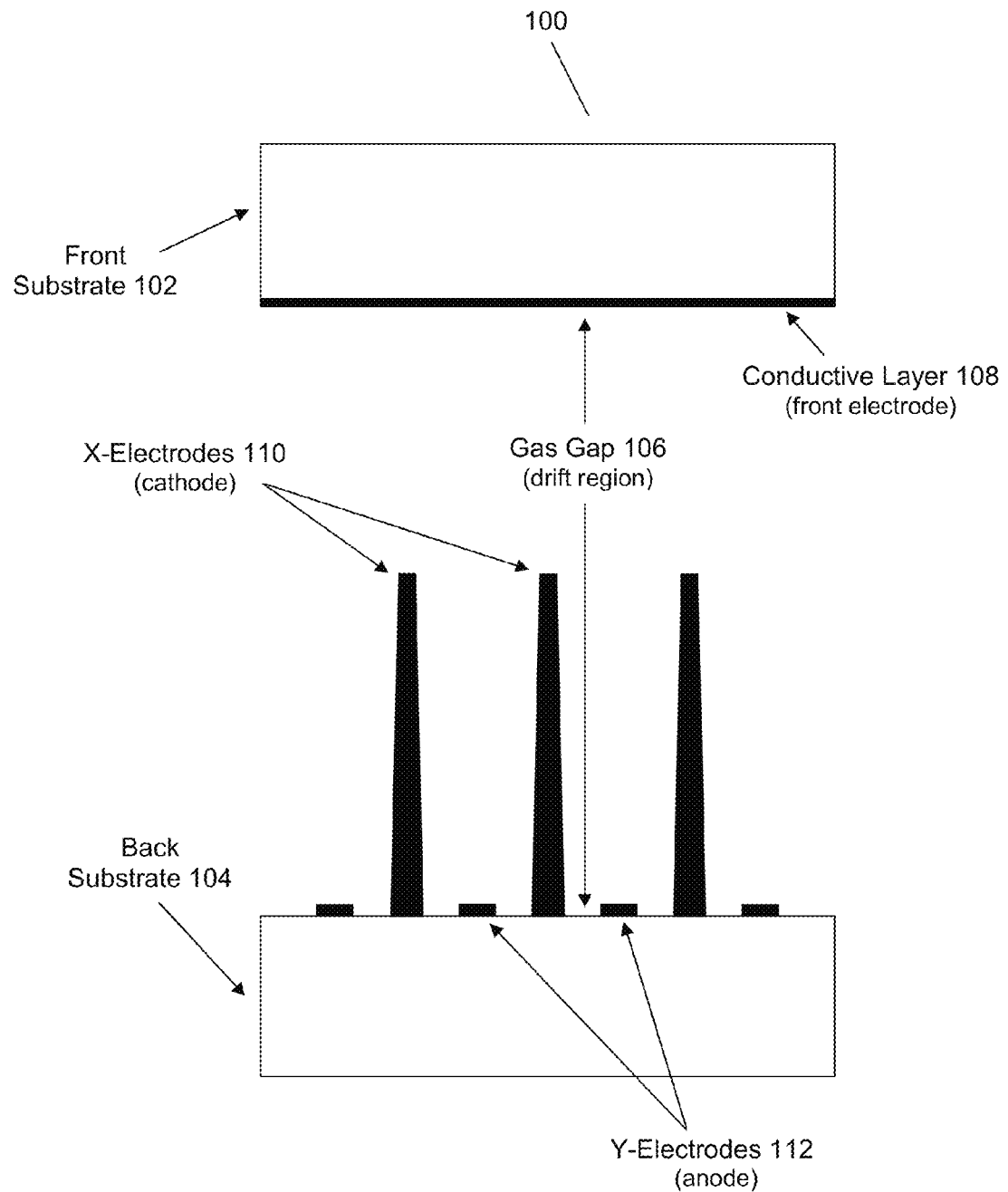
FIG. 5 is a cross-sectional view of an asymmetric vertical wall electrode structure in accordance with one embodiment that can be used with the disclosed detectors.
Figure 6:
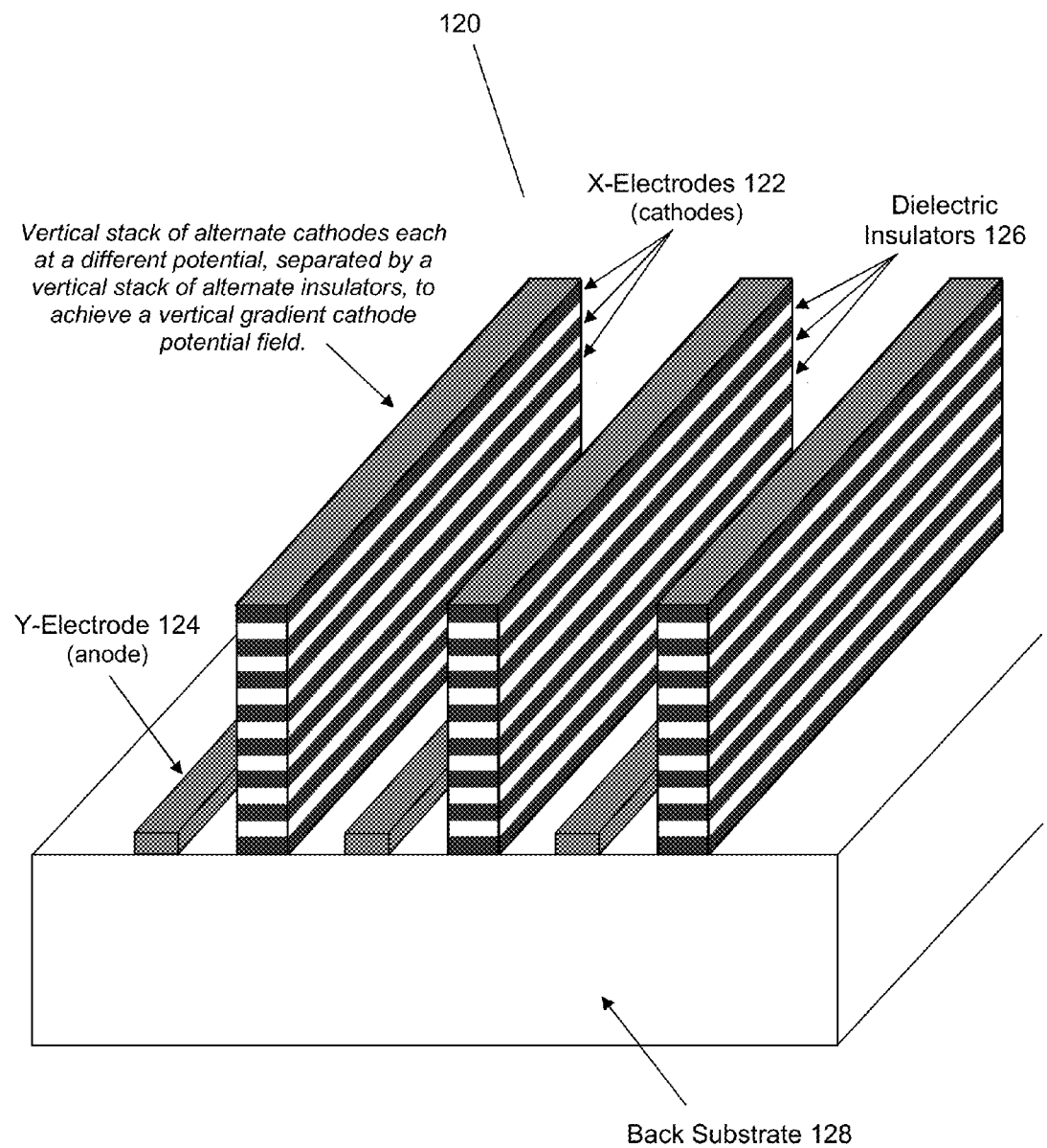
FIG. 6 is a perspective view of an asymmetric multi-potential vertical wall electrode structure in accordance with one embodiment that can be used with the disclosed detectors.

In one embodiment, the avalanche region is extended further into the gas by the use of non-planar discharge electrode structures, such as vertical electrodes extending up from the PPS back plate into the gas towards the drift electrode. FIGS. 3-6 disclose embodiments with such an asymmetric arrangement. FIG. 3 is a cross-sectional view of a barrier wall vertical electrode structure in accordance with one embodiment that can be used with the disclosed detectors. FIG. 3 includes vertical electrodes 72 and flat electrodes 74. FIG. 4 is a cross-sectional view of an asymmetric elevated vertical electrode structure in accordance with one embodiment that can be used with the disclosed detectors. FIG. 4 includes vertical electrodes 92 and flat electrodes 94. FIG. 5 is a cross-sectional view of an asymmetric vertical wall electrode structure in accordance with one embodiment that can be used with the disclosed detectors. FIG. 5 includes vertical electrodes 110 and flat electrodes 112. FIG. 6 is a perspective view of an asymmetric multi-potential vertical wall electrode structure in accordance with one embodiment that can be used with the disclosed detectors. FIG. 6 includes flat electrodes 124 and a stack of vertical electrodes 122 separated by alternate vertical dielectric insulating layers 126. The multi-potential vertical electrode structure 120 shown in FIG. 6 allows the voltage of each vertical cathode layer to be individually set for more precise control of the overall vertical field gradient. In another embodiment, the vertical stack of electrodes 122 with alternate insulating layers 126 shown in FIG. 6 can be replaced by a flat top and bottom strip conductor separated by a uniform vertical resistive wall resulting in a vertical field gradient. In one embodiment the vertical resistive wall can be made non-uniform with respect to its volume resistivity as a function of wall height.

In FIGS. 3-6, only the X-electrodes (i.e., cathodes) extend vertically into the gas gap region while the Y-electrodes (i.e., anodes) assume a flat-wire configuration in the plane of the back substrate. However, in one embodiment this assignment could be reversed with the vertical electrodes being the anodes and the flat electrodes the cathodes. In one embodiment, given a 20:1 aspect ratio and a PPS electrode width of 100 μm, the vertical electrode structure would extend 2.0 mm into the gas drift region. In another embodiment the alternate vertical electrode configuration could be eliminated and both the X- and Y-electrodes could be vertical.

Another embodiment can enhance the collection efficiency by reducing the gas gap distance between the drift electrode and the discharge X- and Y-electrodes, thus increasing the field strength between the drift and avalanche planes, and then compensating for the reduced active gas media volume (i.e., from the reduced gas gap) by increasing the gas pressure. Depending on the ionizing-particles to be detected, the internal gas pressure can be made significantly positive (i.e., well above one atmosphere) without distorting the internal gas gap distance by the use of sufficiently thick substrate plates to contain the gas pressure. Alternatively, an embodiment can use thinner substrates with external reinforcing strips, bars, rods, wires to maintain the flatness of the substrates under a positive internal pressure.

In some embodiments, surface-discharge electrodes can be made by employing multichip module ceramic technology (i.e., MCM-C) on low-cost ceramic, glass-ceramic or high temperature glass substrates (e.g., alumina, silicon nitride, fused silica, boro-aluminosilicate glass, etc.). As one example, to fabricate embedded resistors a thin-film LTCC (low temperature co-fired ceramic) process can be used to produce resistors which with laser trimming can achieve an accuracy of ±1%. Other thin-film and thick film processes with photolithography and wet or dry etching can be used to fabricate vertical resistors under the electrodes, shown in FIGS. 11-14, and depending upon the cell resolution, thick-film printed resistors can also be fabricated within each cell or group of cells with an accuracy on the order of ±1% with laser trimming.

Figure 11:
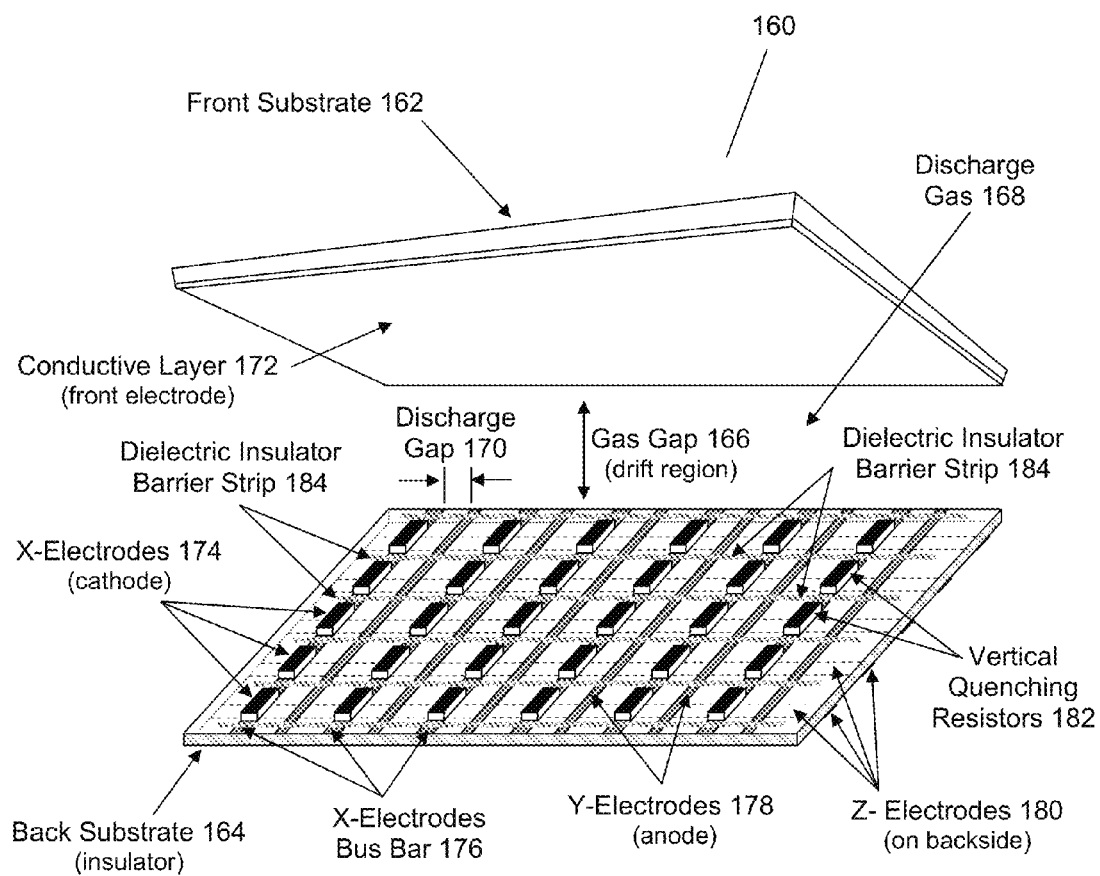
FIG. 11 is a perspective view of a surface-discharge PPS and/or PPPS detector with a segmented surface-discharge electrode pattern on top of vertical quenching resistors and with dielectric barrier strips that cover and electrically insulate the bus bar electrodes in accordance with one embodiment of the present invention.
Figure 12:
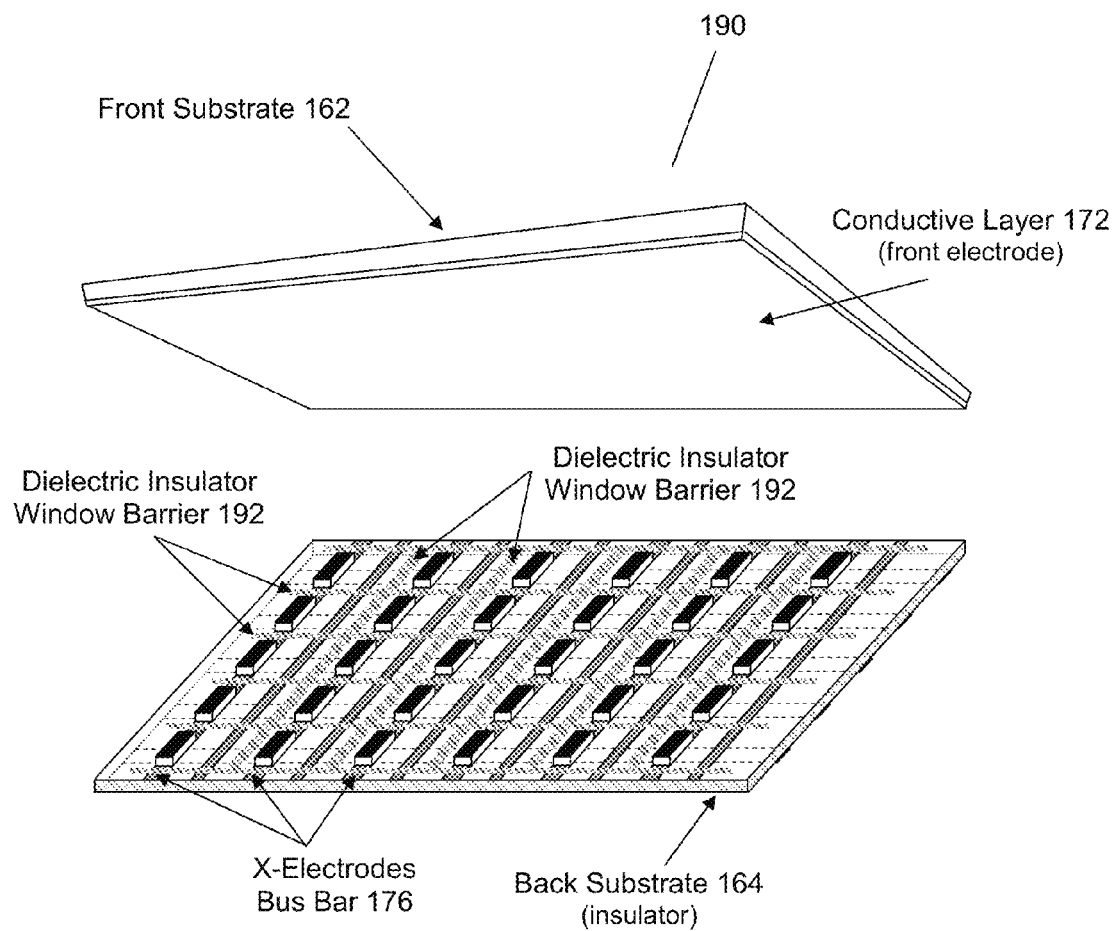
FIG. 12 is a perspective view of a surface-discharge PPS and/or PPPS detector with a segmented surface-discharge electrode pattern on top of vertical quenching resistors and with a flat dielectric window insulator barrier structure that covers and electrically insulates the bus bar electrodes in accordance with one embodiment of the present invention.
Figure 13:
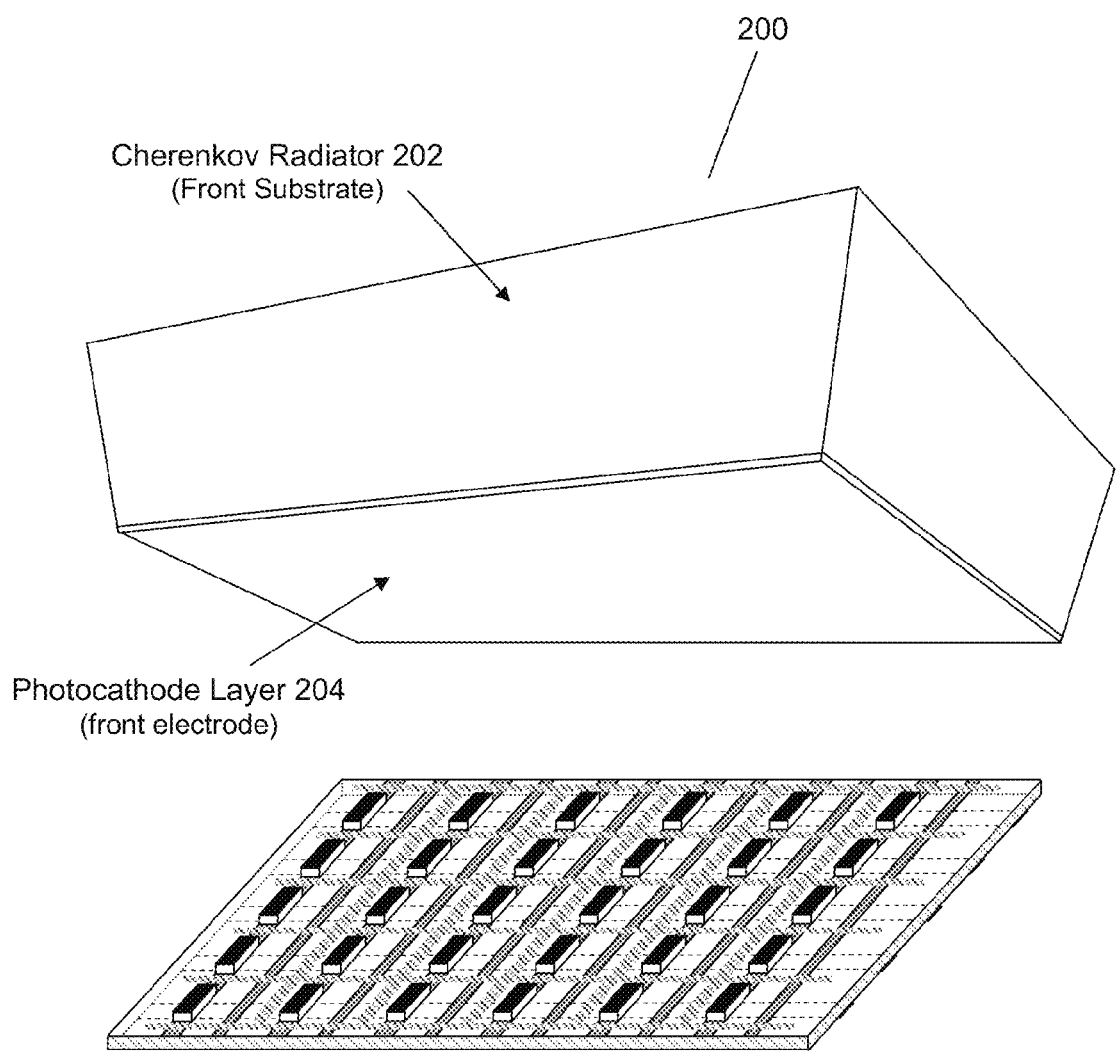
FIG. 13 is a perspective view of a surface-discharge PPPS Cherenkov detector with a segmented surface-discharge electrode pattern on top of vertical quenching resistors and with a flat dielectric window insulator barrier structure that covers and electrically insulates the bus bar electrodes in accordance with one embodiment of the present invention.
Figure 14:
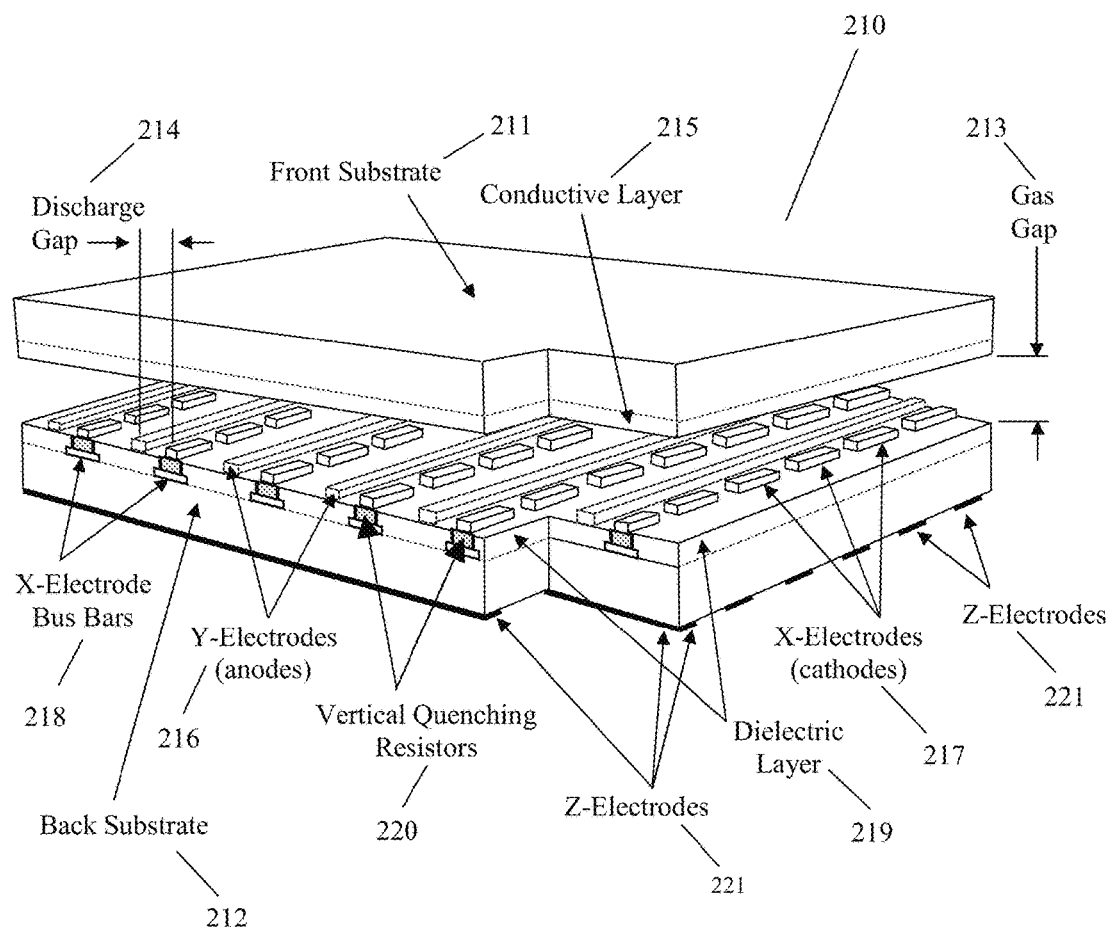
FIG. 14 is a perspective view of a multilayered surface-discharge PPS and/or PPPS detector with a segmented surface-discharge electrode pattern and vertical quenching resistors, and with a flat dielectric insulating layer over the bus bar electrode layer in accordance with one embodiment of the present invention.

FIG. 11 is a perspective view of a surface-discharge PPS and/or PPPS detector with a segmented surface-discharge electrode pattern 174 on top of vertical quenching resistors 182 and with dielectric barrier strips 184 that cover and electrically insulate the bus bar electrodes 176 in accordance with one embodiment of the present invention. FIG. 12 is a perspective view of a surface-discharge PPS and/or PPPS detector with a similar segmented surface-discharge electrode pattern on top of vertical quenching resistors and with a flat dielectric window insulator barrier structure 192 that covers the bus bar electrodes in accordance with one embodiment of the present invention. FIG. 13 is a perspective view of a surface-discharge PPPS Cherenkov detector with a similar segmented surface-discharge electrode pattern on top of vertical quenching resistors and a flat dielectric window insulator barrier structure that covers the bus bar electrodes in accordance with one embodiment of the present invention. FIG. 14 is a perspective view of a multilayered surface-discharge PPS and/or PPPS detector with a segmented surface-discharge electrode pattern and vertical quenching resistors, and with a flat dielectric insulating layer over the bus bar electrode layer in accordance with one embodiment of the present invention. For the embodiments shown in FIGS. 11-14, the X-electrode bus bar is in all cases prevented from itself discharging to the Y-electrode by being covered by a dielectric insulator layer such as the barrier strip 184 in FIG. 11, or the window barrier 192 in FIG. 12 (also shown by itself in FIG. 9). In another embodiment, the X-electrode bus bar 218 is "buried" under the dielectric layer 219 shown in FIG. 14 and connects via the vertical quenching resistor 220 to the surface-discharge X-electrode 217. All of the embodiments for the described PPS and PPPS detectors can be hermetically sealed, gas processed and generally fabricated in a manner similar to PDP devices.

Known PDP-TV monitors have pixel configurations that incorporate internal vertical barrier structures to isolate each cell from adjacent cell interactions, including avalanche spreading but primarily to prevent UV and VUV photon "leakage" from one cell to the next causing adjacent phosphors to be stimulated and thus resulting in RGB phosphor "bleeding" and color de-saturation. Many of these structures literally surround and enclose each cell, thereby preventing all migration of excited species to adjacent cells. Dozens of these vertical barrier structures have been developed, some with height-to-width aspect rations as great as 15:1 to 20:1. These barriers are being developed for PDP-TV sets with widths as small as 12-15 μm (such barriers also serve as the gas gap spacer between the front and back plates) and have been described as broadened knife-edge structures with completely vertical or very slightly trapezoidal-shaped walls. Most PDP barriers have well-defined flat plateau tops while others can be rounded at the edge or the top. Practically every shape imaginable has been fabricated, including geometries described as: diamond, egg-crate, delta, honeycomb, saddle-back, square, rectangular, triangular, pentagonal, hexagonal, U-shaped, cylindrical, hemispherical, etc. A number of barrier fabrication techniques have been developed employing a variety of materials including multilayer composites that could have alternate insulating and conductive layers as shown in FIG. 6. Since most of these barrier wall structures were developed for meter-size PDP TV-sets, they employ low-cost fabrication techniques and low-cost materials. Some of these structures have been made of conductive materials, and all of them could be coated with a thin-film metallization layer to create what the PDP industry calls vertical wall or barrier wall electrodes which have been demonstrated to exhibit high efficiency. In some embodiments of PPS 10, for example, the use of elevated vertical electrode structures can result in a higher efficiency, well-behaved, avalanche/discharge field that extends well into the gas and thus produces a significantly improved, higher performance detector when compared to the traditional "flat" micropattern electrodes that essentially reside in the substrate plane.

Figure 2:
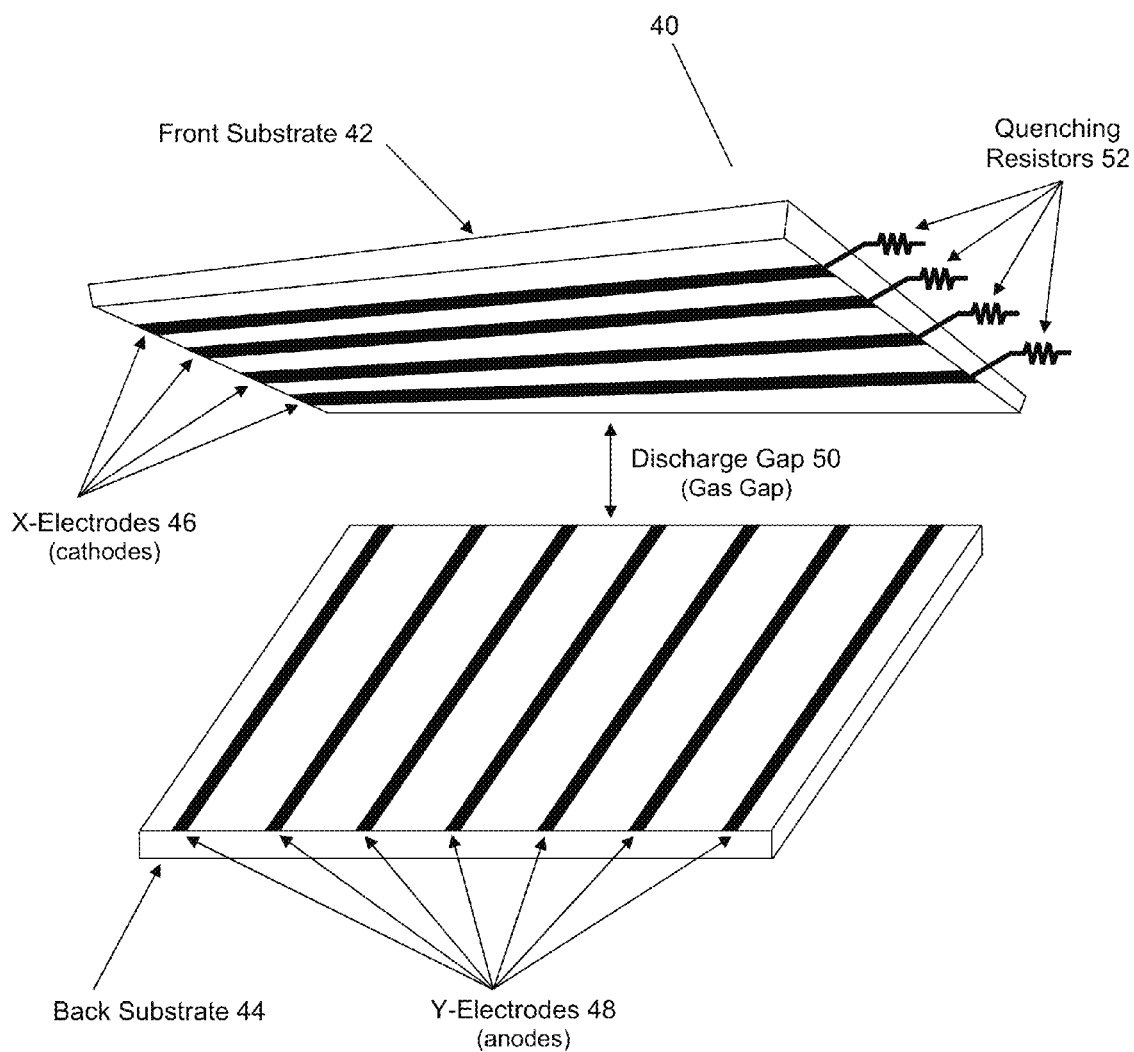
FIG. 2 is a perspective view of a columnar-discharge PPS and/or PPPS detector with an orthogonal electrode pattern that includes electrode line quenching resistors in accordance with one embodiment of the present invention.

Embodiments include a large number of PPS and PPPS electrode device structures (both AC and DC) with a variety of X-Y (i.e., 2-electrode, and 3-electrode if combined with a drift electrode, conversion electrode or photocathode) and X-Y-Z (i.e., 3-electrode, and 4-electrode if combined with a drift electrode, conversion electrode or photocathode) configurations. One such example of a 2-electrode X-Y structure is detector 40 shown in FIG. 2, which is a perspective view of a columnar-discharge PPS and/or PPPS detector with an orthogonal electrode pattern that includes electrode line quenching resistors 52 in accordance with one embodiment of the present invention. In this embodiment, X-electrodes 46 and Y-electrodes 48 are perpendicular to each other and on opposite substrates 42 and 44, and in their orthogonal orientation have some similar elements as DC- and AC-PDP's produced through the early-1990's (and disclosed, for example, in U.S. Pat. No. 7,518,119). Both the columnar and surface-discharge structures can include quenching resistors as shown in FIGS. 1 and 2. For the columnar structure embodiment of FIG. 2, one quenching series resistor 52 is used for each X-electrode line 46 (cathode). For the surface-discharge embodiment of FIG. 1, one quenching series resistor 30 is used for each discharge cell off of the cathode line 24. In another embodiment of the surface-discharge structure, one quenching series resistor is used for each X-electrode line instead of each X-electrode cell in FIG. 1.

Further, the surface-discharge electrode embodiments shown in FIGS. 1 and 11-14 can be used not only for ionizing-particle PPS's, but also for light-sensitive PPPS detectors by incorporating a photocathode for the front conductive layer for most of the embodiments disclosed above and as shown for the "Cherenkov" PPPS detector in FIG. 13. For all of the embodiments described herein, the designation of "front" and "back" is arbitrary, meaning that all of the embodiments can be used with the top and bottom or front and back reversed with respect to the incident radiation direction.

For all PPS and PPPS embodiments, whether surface-discharge or columnar-discharge, there is a cathode (e.g., X-electrode) and anode (e.g., Y-electrode). Either electrode can function as the power electrode. In many embodiments, the cathode is biased negatively by the power supply and operated as the discharge electrode. The anode would then generally be operated at or near ground and would be monitored as the signal sense electrode. In a 3-electrode, surface-discharge configuration, the 3rd electrode, or Z-electrode would be deposited orthogonal to the X and Y surface-discharge electrodes, most conveniently on the backside of the surface-discharge substrate (as shown in FIGS. 1, 7-8, 11-14 and 16) and capacitively couples through the substrate to the discharge pulse created at the X-Y cell avalanche site. In order for the Z-electrode to acquire a good signal, the substrate is a dielectric and is generally limited to a maximum thickness of a few millimeters, with thinner typically being better. Operationally, the specific Z-electrode that picks up the strongest signal would serve to locate the orthogonal intersection that defines the specific X-Y cell discharge position. In the 4-electrode surface-discharge embodiment, the 4th electrode can be a metal drift electrode (i.e., surface front electrode), which serves primarily to vertically shape the drift field and thereby "push" the radiation generated gas ions towards the X-cathode while also "pushing" the radiation generated free-electrons towards the Y-anode. Normally the potential of the drift electrode would be set a little more negative than the cathode. In other embodiments, the absolute bias values are not fixed and so the cathode could be set at essentially any potential value with the anode biased at a suitably higher voltage in the positive direction. For a given electrode discharge gap and gas pressure, there will be a minimum voltage required for gas breakdown (i.e., the firing voltage) for a given gas composition, and this minimum voltage can be plotted as a function of pd (i.e., pressure times distance of anode-cathode separation gap). The resulting plot is known as the "Paschen" curve, and can be used to estimate the required anode-cathode bias setting for a given PPS or PPPS device.

For the PPPS embodiment, one benefit of the surface-discharge electrode structure is that by moving the X-electrodes 46 from, for example, the front substrate in the columnar embodiment of FIG. 2, to the back substrate in the surface-discharge embodiments of FIGS. 1 and 11, the conductive electrode layer 22 in FIG. 1, or layer 172 in FIG. 11, can function as an efficient photocathode with essentially a 100% fill-factor. However in one embodiment the columnar-discharge embodiment of FIG. 2 can be configured as a PPPS, albeit with a reduced fill-factor, by the use of a robust, dual purpose X-electrode conductor that is also a photocathode, such as a thin-film Au (e.g. ~0.1 μm thick) or fluorine-doped $SnO_2$ transparent photocathodic conductor.

Figure 7:
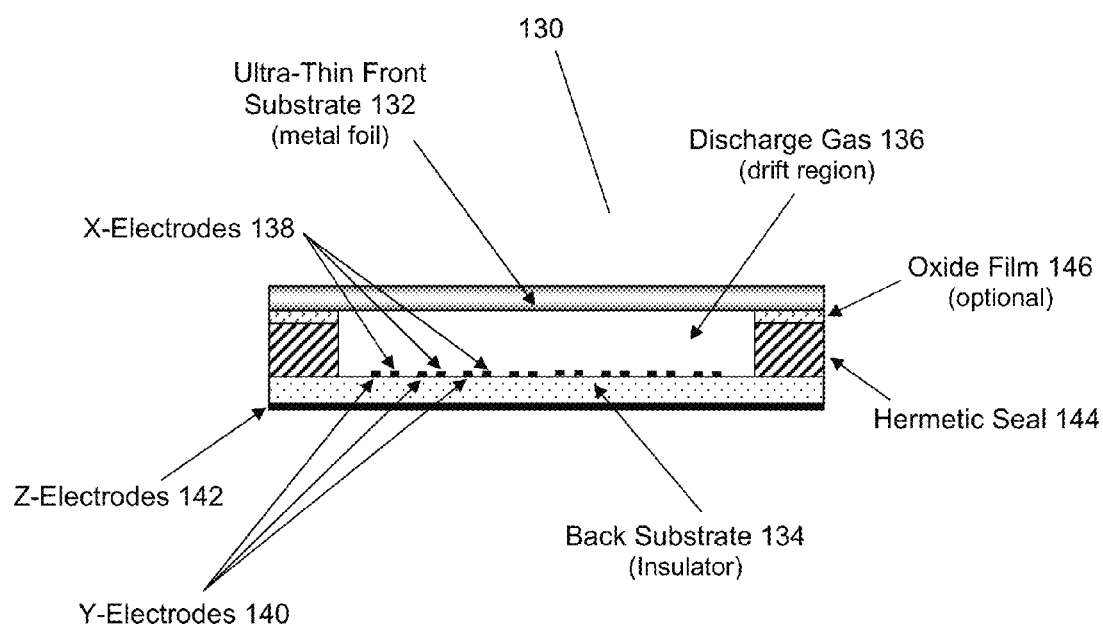
FIG. 7 is a cross-sectional view of a surface-discharge PPS and/or PPPS detector with a metal-foil front substrate and a parallel/rectilinear surface-discharge electrode pattern on the back substrate with an orthogonal back electrode pattern in accordance with one embodiment of the present invention.
Figure 16:
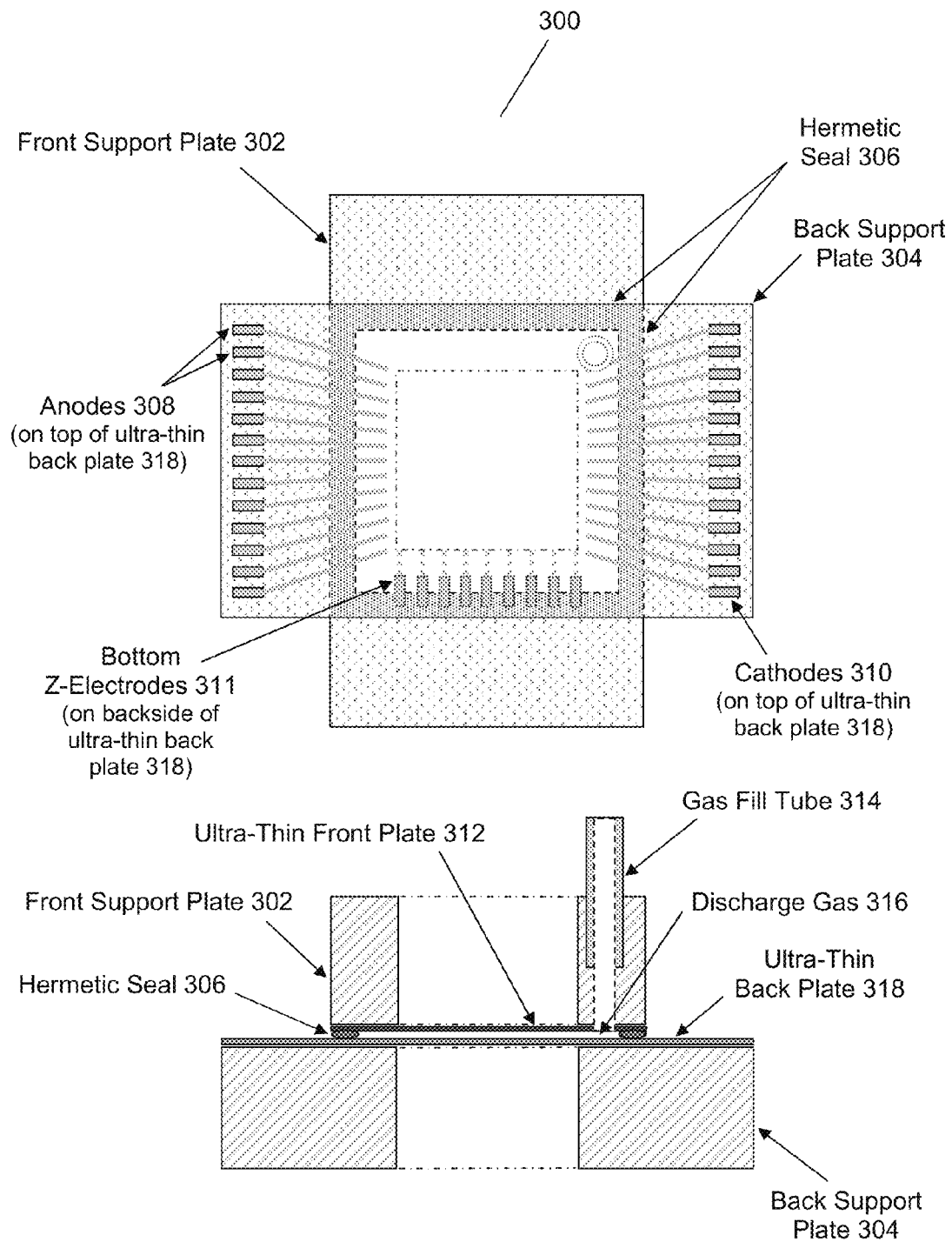
FIG. 16 is a cross-sectional view of a surface-discharge PPS detector with ultra-thin front and back substrates in accordance with one embodiment of the present invention.

For those embodiments which do not have a photocathode, the surface-discharge electrode structure significantly improves device efficiency because it allows 100% surface coverage by a front plate drift electrode. It also facilitates the use of a dual purpose design in which a metal thin-foil could be used as both the front cover plate and the drift electrode as shown in FIGS. 7 and 16 below. FIG. 7 is a cross-sectional view of a surface-discharge PPS detector with a metal-foil front substrate 132 and a parallel/rectilinear surface-discharge electrode pattern (i.e., X-electrodes 138 and Y-electrodes 140) on the back substrate with an orthogonal backside Z-electrode pattern 142 in accordance with one embodiment of the present invention. FIG. 16 is a cross-sectional view of a surface-discharge PPS detector with both ultra-thin front and back substrates in accordance with one embodiment of the present invention.

By using a thin-foil cover plate as shown in FIGS. 7 and 16, the reduction in front substrate mass and thickness leads to enhanced device efficiency, especially for applications involving large atom-sized, ionizing-particles (e.g., PPS Active Pixel Beam Monitor for radioactive ion beam profile diagnostics) that are easily stopped via interaction with the front substrate and thus are very sensitive to the front substrate mass. However, a metal foil cover plate embodiment as shown in FIGS. 7 and 16 is also advantageous for the detection of smaller ionizing particles, such as for proton, carbon ion and neon ion beams used in hadron particle beam therapy, in which the minimization of particle beam scattering by the detector is critical. Such applications thus require very low mass detectors which could greatly benefit by an ultra-thin front and back substrate structure such as that in FIG. 16 based on metal foils or flexible sheets made from ceramic, glass, semiconductor, or crystalline type materials on the order of about 0.001 inches thick and preferably less. Examples of suitable foils include metals or metal alloys of aluminum, titanium, stainless steel, nickel, iron, copper, cobalt, beryllium, magnesium and molybdenum, and superalloys such as 0.00025" thick Arnavar™ foil (i.e., Co—Cr—Fe—Ni alloy made by Arnold Magnetic Technologies) and Inconel foil. Examples of other ultra-thin substrates include materials such as alumina, sapphire, fused silica, silicon, glass, silicon nitride, etc., which can all be fabricated in thicknesses of less than 0.001 inches. In one embodiment, an "ultra-thin substrate" would include any substrate having a thickness between approximately 1-300 microns, or 0.001-0.3 mm, thick.

An additional advantage of the surface-discharge design is that with the two discharge electrodes (i.e., X and Y) located on the back substrate, the gas gap is independent of the discharge gap, as the latter is solely a function of the quality of the X-Y electrode lithography on the back substrate. Thus for the surface-discharge structure, the device uniformity should be far better than in the columnar-discharge design. In addition, a much larger gas-gap can be employed without compromising the device spatial resolution since the gas gap and discharge gap are completely decoupled in the surface-discharge configuration. Finally for PPS and PPPS detectors, including both columnar and surface discharge electrode embodiments, the choice of the electrode metal may be important in terms of device performance and device lifetime. With regard to device lifetime, for DC discharge devices in which the bare electrode is in direct contact with the plasma, which means subject to hot electrons and ion sputtering, the electrode material should have a high melting point and be sputter resistant. This means that ideally the selected metal should have some level of refractory character, while being chemically resistant to the discharge gas including possible chemical species created in the plasma. Also the selected metal should not be a catalyst for gaseous reactions in the plasma, nor should it contain significant amounts of radioactive isotopes. Other considerations include photocathodic activity and device fabrication process compatibility. Given the above considerations, two examples of suitable electrode metals for most PPS and PPPS device applications are Ni and Cr.

Cell Dielectric Isolation

Embodiments can use a number of methods to minimize adjacent cell crosstalk and prevent avalanche spreading to neighboring cells. These methods include the use of avalanche quenching gaseous components added to the discharge gas mixture, the use of internal cell series quenching resistors, and the use of a physical cell dielectric isolation barrier. As an example of such barriers, FIG. 10 is a perspective view of a 3-dimensional vertical barrier structure 156 in accordance with one embodiment that can be used with the disclosed detectors. FIG. 9 is a perspective view of a flat dielectric insulator window barrier structure 152 in accordance with one embodiment that can be used with the disclosed detectors, and implemented as the flat dielectric insulator window barrier 192 shown in FIG. 12. For detector 190 shown in FIG. 12, in one embodiment the 3-dimensional vertical barrier structure 156 can be substituted for the flat window barrier 192. Other examples of dielectric isolation include the embodiment in FIG. 11 which has an array of narrow 2-dimensional flat dielectric barrier strips 184.

The use of physical dielectric barrier structures for achieving cell isolation (i.e., discharge confinement or localization) is applicable to both surface-discharge and columnar-discharge PPS and PPPS device embodiments. In terms of physically confining the radiation induced plasma avalanche to the initial cell gas discharge site, there are two basic approaches used in commercial PDP's that can each be employed in two different embodiments of the PPS and PPPS. The first method is to physically surround each individual cell or an entire electrode line of cells within a barrier wall structure such as wall structure 156 in FIG. 10, which if vertically tall enough could also serve as a three-dimensional support matrix that both defines and maintains a uniform gas gap between the front and back substrates. Dozens of differently shaped barrier wall structures have been successfully employed, from a simple parallel wall configuration to much more complex polygon shaped enclosures (e.g., triangles, squares, rectangles, diamonds, hexagons, honeycombs, saddlebacks, etc.). Generally these 3-dimensional vertical barriers have been used primarily on AC type PDP structures for TV-set applications. In one embodiment the barrier wall structure can also function as a barrier electrode such as the X-electrode 72 of FIG. 3. For the much less complex DC type PDP structures, which for the most part employ a simple double substrate, orthogonally configured, columnar-electrode structure, a low profile (i.e., 2-dimensional) "flat" dielectric pattern can be used to confine the discharge to the local cell site. Accordingly, for the columnar-electrode PPS shown in FIG. 2, in one embodiment, a thick-film dielectric layer is screen-printed over the metal electrodes on the back substrate, with an "open" window area as shown in FIG. 9 located at the X-Y electrode intersection of each pixel site. In this embodiment the open window in the dielectric insulator layer 154 shown in FIG. 9, that is patterned on the back substrate 44 of FIG. 2, leaves the "bare" Y-electrodes 48 exposed to the discharge gas in the discharge overlap region defined by the corresponding orthogonal X-electrodes 46 on the front substrate 42.

Vertical Quenching Resistor Structure for Pixel Isolation

One embodiment uses internal cell series quenching resistors to achieve pixel isolation. An avalanche can be prevented from spreading to adjacent cells by using an appropriate electrode line resistor, for example one resistor for each discharge electrode line connected to the power. These resistors can vary anywhere from the kΩ to MΩ range, depending on the electrode structure, device size and capacitance, pixel resolution, gas composition and pressure, etc. For the more general case in which each pixel has its own embedded series resistor to limit or quench the discharge, there are at least two basic embodiments—the laterally located quenching resistors 30 located in the same plane as the cell electrodes as shown in FIG. 1, and the vertically located quenching resistors 182 in FIGS. 11 and 220 in FIG. 14 located immediately beneath the discharge X-electrodes (174 in FIGS. 11 and 217 in FIG. 14), and immediately above the bus-bar X-electrodes (176 in FIGS. 11 and 218 in FIG. 14). The more space efficient embodiment associated with a higher cell fill-factor is the vertically configured resistor located directly under the discharge electrode (i.e., cathode), which can be employed for both the various columnar-discharge and surface-discharge PPS embodiments. However, in the case of PPPS embodiments, the described vertically configured resistor under the discharge electrode is most conveniently employed for the surface-discharge structure.

For the embodiment shown in FIG. 11, the segmented top discharge X-electrode (cathode) 174 is connected to an underlying contiguous cathode bus-bar X-electrode 176 through the vertical quenching resistor 182, so that each cell has its own dedicated series resistor that effectively isolate it from every other cell connected to the same bus-bar X-electrode line 176. Sensor 160, referred to as the "segmented cell structure", can be used for both PPS (e.g., FIG. 11) and PPPS detectors (e.g., FIG. 13). The most convenient shape in terms of fabrication for the vertical resistive strip located directly under the segmented discharge electrode is that the dimensions of the resistive strip 182 exactly replicate that of the segmented discharge electrode 174 as shown in FIG. 11 as well as FIGS. 12-13. However in the alternative embodiment shown in FIG. 14, a dielectric insulator layer 219 covers the "buried" X-electrode bus-bar 218 structure which connects to the segmented top layer surface-discharge X-electrodes 217 through the vertical quenching series resistor 220. One advantage of the segmented cell structure is that the pixel quenching resistor does not take up any lateral cell space since it is a vertical structure, thus the discharge cell fill-factor should be extremely high, resulting in higher device efficiency.

Primary and Secondary Conversion Layers

The PPS embodiments in FIGS. 1, 11, 12 and 14, with an appropriate conversion layer material, used for the conductive layers 22, 172 and 215 respectively, can be configured as an efficient thermal neutron detector that can rival or even exceed the performance of $^3$He based neutron detectors in many respects, and surpass $^3$He based detectors in high pixel resolution and fast response time with time-of-flight (TOF) capability. The elements Li, B and Gd are all suitable materials for this conversion layer due to having reasonably abundant isotopes (e.g., $^6$Li, $^{10}$B, $^{155}$Gd and $^{157}$Gd) that undergo efficient thermal neutron capture followed by detectable particle emission in a PPS device. For the above embodiments, the efficiency of the PPS as a neutron detector using these materials can be further enhanced by using either isotopically enriched mixtures or highly enriched mixtures of these materials (Li, B and Gd) for the conversion layer. However the preferred element for the PPS conversion layer for many neutron detector applications is Gd, with naturally occurring isotopes $^{155}$Gd and $^{157}$Gd which have amongst the largest thermal (i.e., 0.025 eV) neutron capture cross sections of any isotopes, approximately 61,000 and 254,000 barns, respectively. The naturally available metal, in which $^{155}$Gd is 14.8% and $^{157}$Gd is 15.7%, has an (n, γ) cross section of 49,000 barns. These high cross sections, much higher than that of the popular $^3$He (n,p) reaction (5300 barn), allow embodiments of a Gd-based PPS detector to have many important commercial applications, including homeland security.

The design parameters of a Gd-based detector are derived from the physics of the capture cross section and the resulting decay of the daughter nucleus. The optimum conversion layer thickness will depend on the isotopes chosen, including designing for the naturally available metal. For example, if pure $^{157}$Gd were to be used, then its cross section of 254,000 barns corresponds to a mean free path for the neutron of 1.3 μm. To stop 99% of the neutrons would require a thickness of 6.0 μm, which can be deposited for example by conventional sputtering on an ultra-thin, low density, low atomic number, substrate (e.g., thin-film polymer or aluminum foil) to minimize scattering losses from the emitted conversion electrons (see below). For $^{155}$Gd or $^{nat}$Gd, the corresponding 99% neutron absorption thickness is ~0.001", which is within the range of commercially available Gd-foils. Several embodiments of the PPS detector can utilize a metal foil electrode that also serves double-duty as the device front substrate. Two of these embodiments are shown in FIGS. 7 and 16, which are ideal for a Gd-foil based PPS neutron detector, but could also be used for $^6$Li and $^{10}$B foil based PPS neutron detectors. For neutron detector 130, shown in FIG. 7, the Gd-foil electrode 132 would be hermetically sealed directly to a significantly thicker surface-discharge back substrate 134 that would provide the required mechanical support. In one embodiment, the fabrication of the Z-electrodes 142 is optional and may not be needed. For neutron detector 300, shown in FIG. 16, the Gd-foil electrode would serve as the ultra-thin front plate 312 and would hermetically seal to a thin or ultra-thin back plate 318, thus enabling high transmission of gamma radiation through the device that could be efficiently detected behind it, and then by timing coincidence used to help discriminate incident thermal neutrons from incident gamma radiation. It is noted that for detector 300, mechanical support for the ultra-thin front and back plates is provided by sealing the thick front support perimeter plate 302 to the thick back support perimeter plate 304 as shown in FIG. 16. Also, as disclosed above for detector 130 in FIG. 7, the fabrication of the bottom Z-electrodes 311 for detector 300 is optional and may not be needed.

In terms of detecting the neutron capture for $^{157}$Gd, the daughter nucleus, $^{158}$Gd, decays by emitting a number of gamma rays that easily escape the foil. However, 59% of the neutron capture events cause an electron to be emitted from the nucleus, through internal conversion, with energy around 75 keV. About 7% of the time, a second electron is emitted with energy of 181 keV. An electron with 75 keV will lose 12 keV, on average, of energy in traversing the entire 6 μm foil. If the foil is at the window of the detector as in FIG. 7, about half the electrons will enter the sensitive gas volume, for a net efficiency of about 30%. This means that of all the neutrons stopped in the foil, about 30% can potentially be detected. This efficiency, however, can be approximately doubled for the embodiment shown in FIG. 8 of a double surface-discharge PPS detector 150 with a central conversion layer 149 shared between a top and bottom set of parallel/rectilinear surface-discharge X and Y-electrodes 139. Thus for PPS detector 150, the $^{157}$Gd-foil conversion layer 149 efficiency can essentially be doubled to nearly 60% when located between the two surface-discharge PPS back plates so as to detect electrons emitted into the gas volume from the Gd-foil in all directions. These values compare very favorably with $^3$He detectors, which can be as efficient as 70%. Additional embodiments could employ multiple layers of PPS detectors utilizing thinner Gd-foil to increase the detection efficiency above 60% by detecting in addition to the conversion electrons, other fast electrons between 29 and 79 keV produced by Auger transitions. For detector 150, the Z-electrodes 142 located on both the front and back substrates are application specific and therefore optional.

Regarding the response of the above detector embodiments, Gd is an excellent detector for thermal neutrons, far more efficient than $^3$He (n,p). Yet for energies above 1 eV, the Gd neutron cross section falls below $^3$He. Nevertheless, the use of Gd near and below thermal energies should be an excellent replacement for $^3$He for many critical applications. It is noted that a hydrogenous moderator such as paraffin or polyethylene will be utilized to convert the incident fast neutrons to slow thermal neutrons for maximum detection efficiency. The disclosed Gd-foil based PPS neutron detectors, require detecting the fast conversion electrons emitted by the Gd in the PPS discharge gas, which is symmetrical to detecting a positively charged muon in the PPS. Careful system design including critical materials selection will result in a high efficiency system with high gamma discrimination. Embodiments of The PPS detector, because of its extremely fast response time, could be used to advantage with active interrogation techniques to reduce background signals by coupling the interrogation pulse to the PPS detector response so as to record only the coincidence readings. In addition, with a pixel pitch of 50-100 µm, its very high pixelation granularity allows discrimination of different size discharge cluster patterns from different incident source radiations. These capabilities are further aided by the addition of a gamma filter such as lead in front of the detector should it prove necessary.

Figure 8:
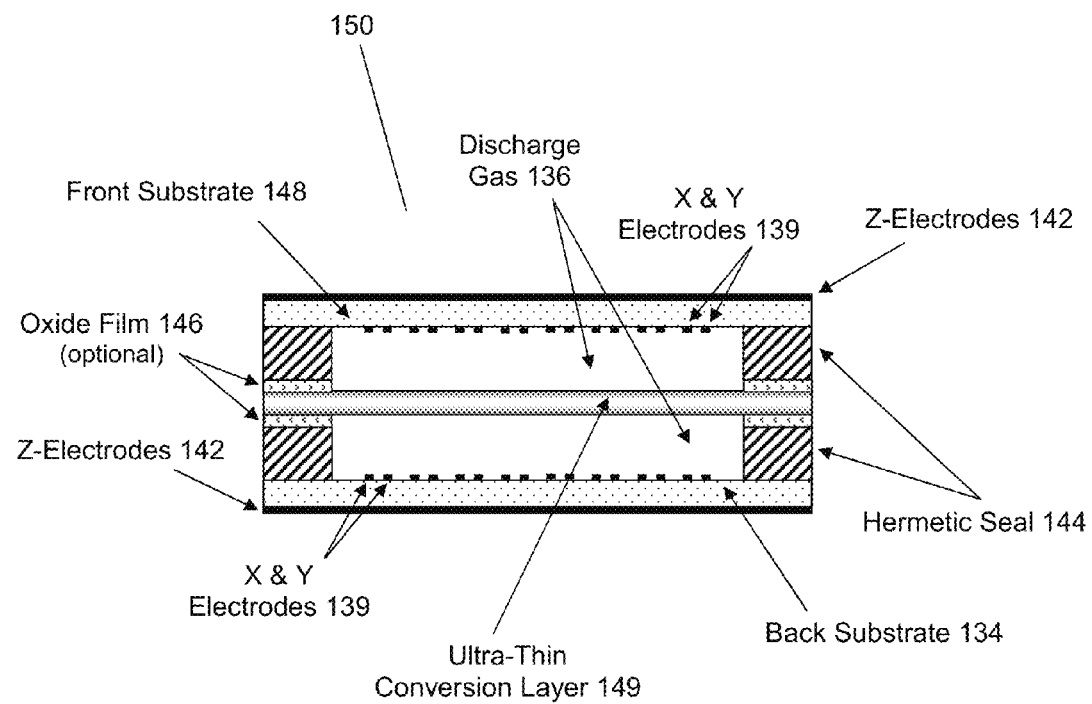
FIG. 8 is a cross-sectional view of a double surface-discharge plasma panel radiation detector with a central conversion layer shared between and the top and bottom sets of parallel/rectilinear surface-discharge electrodes in accordance with one embodiment of the present invention.

In one embodiment for the detector shown in FIG. 8, in which the discharge gas 136 is at a significant positive pressure (e.g., 10 atmospheres), then the front substrate 148 and back substrate 134 would need to be thick enough and strong enough to contain this pressure without significant physical/dimensional distortion. For this detector embodiment, the front and back substrates could be a heavy metal such as steel which would also have the benefit of being a partial gamma filter. Given such a metal substrate, a dielectric insulator layer (e.g., enamel on steel) would be coated on the inside surface facing the gas on which the X and Y-electrodes would then be fabricated.

Materials selection for device fabrication will utilize a low neutron absorption cross-section conductor with low background emission such as copper (or Ni or Cr), with a flash coating of a sputter resistant low neutron absorption cross-section metal such as Mo, Ni or Cr for the device electrodes, in combination with a low neutron absorption and low background emission substrate such as fused silica or possibly an alumina, zirconia (i.e., MgO or yttria stabilized zirconia—YSZ) or a magnesia based ceramic with low alkali content (e.g., cordierite or mullite).

The disclosed Gd-based PPS neutron detector embodiments can utilize thin-film deposited Gd coatings from several microns thick, to thin foils in the range of 0.001", with a pixel pitch from about 0.1 mm to 10 mm, an external thick polyethylene or other such hydrogenous moderator, and a gas discharge mixture composition including gas components such as Ne, Ar, Kr, Xe, N$_2$, Hg, CO$_2$, CH$_4$, O$_2$H$_6$, CF$_4$ and C$_2$F$_6$, with gas pressures over the range from about 0.1 to 10 atmospheres. Other embodiments not shown include the same primary Gd conversion material as described above, but with the addition of a thin-film (e.g., less than 1 µm) of high secondary electron emitter material coated on top of the Gd primary conversion layer to generate a cluster of slower secondary electrons, from each Gd primary conversion electron, into the discharge gas volume that can more easily be detected and thereby further enhance the detector efficiency. Examples of secondary electron emitter thin film coatings for this application include: CsI, MgO, BaO, La$_2$O$_3$, Eu$_2$O$_3$, LiF, CaF$_2$ and BaF$_2$. The Gd-based PPS neutron detector is suitable for both passive and active interrogation applications and could be used to detect special nuclear materials (SNM) such as plutonium.

The PPS detector shown in FIG. 8 and disclosed above can also be constructed to be a high efficiency PPPS detector. In one such embodiment, the conversion layer 149 would consist of a very thin photocathode layer deposited on both the top and bottom surfaces of an optically-transparent substrate. The dual photocathode conversion layer 149 would therefore be emitting photoelectrons on both surfaces towards both sets of surface-discharge electrodes 139. For this dual surface photocathodic coating, the top photocathode layer would be functioning primarily as a reflective photocathode, whereas the bottom layer would be functioning primarily as a transmissive photocathode. For all PPPS embodiments, the front substrate is optically transparent and could be made of either glass or fused silica, although other transparent substrate materials such as sapphire and MgF$_2$ could also be employed. For maximum PPPS efficiency, the front substrate X, Y and Z electrodes should also be transparent and so would employ a transparent conductor such as ITO or SnO$_2$.

Cherenkov Detector

PPPS embodiments disclosed above can be readily configured as Cherenkov detectors by careful selection of the PPPS photocathode to the selected Cherenkov radiator, and optically coupling the two components together. However a more efficient Cherenkov detector can be fabricated by effectively making the Cherenkov radiator the PPPS front substrate window—that is integrating the two components into a single PPPS Cherenkov Detector. In this combined device, disclosed in FIG. 13, the PPPS front substrate window will as a result be much thicker. However, the choice of window material for the Cherenkov radiator will be largely governed by the choice of photocathode. For example, if a robust VUV photocathode such as CsI is chosen, then the PPPS front substrate window/Cherenkov radiator will likely be MgF$_2$ or possibly CaF$_2$, but the radiator could also be sapphire or fused silica if the emitted photons are in the VUV region closer to the UV. If on the other hand the PPPS photocathode is a longer wavelength UV or blue sensitive material, then the PPPS front substrate/Cherenkov radiator can be either fused silica or a highly blue transmissive glass.

Vertical Electrode Structures

In order to enhance the drift field effectiveness and more efficiently channel the radiation generated free-electrons to the sense anode (Y-electrode) and the ions to the discharge cathode (X-electrode), in one embodiment the drift field can be custom configured by use of vertical electrodes that extend well up into the drift field region. Such vertical electrodes structures have been demonstrated in PDP's developed for TV-sets and are generically known as barrier electrodes. A variety of vertical electrode or barrier electrode shapes and cross sections have thus been fabricated by well-established commercial processes, such as direct thick-film printing, or thick-film coating followed by pattern etching or pattern sandblasting, etc. These techniques also allow multiple layers of different conductivities or resistivities to be fabricated, including alternate layers of conductors, resistors and insulators so that the vertical electrode can have different layers biased at different potentials to optimize the drift field shape to the application, such as shown in FIG. 6. Alternatively, a single vertical conductive barrier can be thick-film fabricated or a vertical dielectric barrier fabricated and then thin-film coated with a conductor to make it into a vertical electrode. Finally, the vertical electrode can be configured to extend either partially into the drift field (as shown in FIGS. 4 and 5) or all the way up to the front cover plate. In the latter case, the vertical electrode in one embodiment has a top insulator layer (see FIG. 3) so that the vertical electrode does not electrically short out the drift electrode in the case of a PPS, or electrically short out the photocathode in the case of a PPPS. However in one embodiment, the drift electrode or photocathode is at the same potential as the vertical cathode, so making electrical contact between the vertical electrode and the drift electrode or photocathode in this case is acceptable.

Ground Planes and Shielded Electrode Traces

Since embodiments of the PPS and PPPS are very fast response detectors with some applications requiring sub-nanosecond and picosecond scale temporal resolution, such as for time-of-flight (TOF) detection and Cherenkov detectors, the circuit layout for these PPS and PPPS devices can take advantage of standard industry practice by incorporating the addition of appropriately located ground planes and the aggressive shielding of electrode lines, traces, wiring, ribbon cabling and connectors and other components wherever feasible.

Electronic Circuitry and Readout

Embodiments of PPS and PPPS devices operate as highly-pixelated digital radiation detectors by flashing "ON" each pixel (which is normally "OFF") as a direct consequence of a gas discharge avalanche stimulated within the cell by incoming radiation, and so at their most basic level functionally behave as digital radiation counters and not as proportional counters. Each such gas discharge pulse is counted as having an approximately equal value and is therefore counted by the circuit as simply an individual event. The amount of detected radiation is thus based on how many individual gas discharge events are outputted from the pixels. The electronic readout circuitry is thus designed to detect if and when a gas discharge pulse is outputted from the pixel—i.e. when a pixel has turned "ON". In order to maximize the temporal resolution, the readout circuitry preserves the cell discharge output pulse rise time.

On both an operational and functional basis, all such radiation induced pixel discharges begin (i.e., are turned "ON") by initially maintaining the panel at a voltage just below its spontaneous discharge setting, such that any free-electron upon entering the gas can "immediately" set off a discharge (at the nearest pixel site) that can very quickly grow into a localized high-gain avalanche. The rise time for such fast discharges can typically vary from a few nanoseconds to a few picoseconds, depending upon the effective cell capacitance, which includes the contributions from the matrix of capacitively coupled surrounding cells. The previously disclosed embodiments include a variety of electrode structures and material choices including special gas mixtures and physical barriers to optimize performance and localize the discharge including minimizing plasma generated interference from photons, electrons, ions and metastables.

Figure 15:
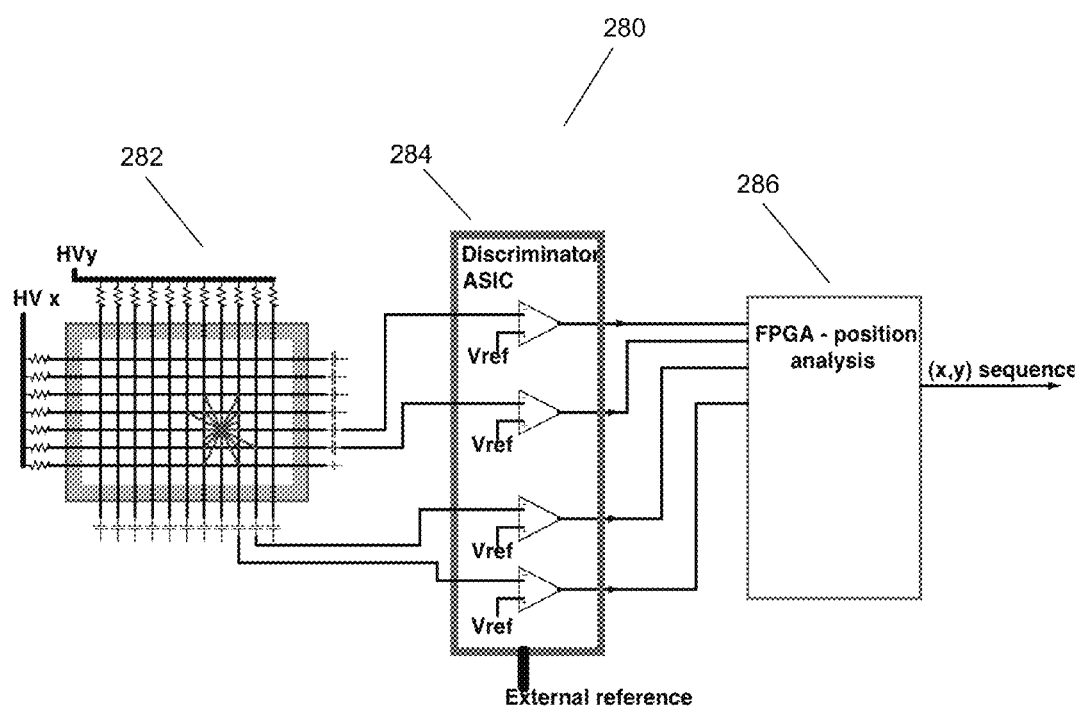
FIG. 15 is a block diagram of a counting circuit in accordance with one embodiment of the present invention.

In one embodiment, the pixel sensing mechanism includes digital (i.e., photon/particle counting) acquisition electronics to store time-tagged pixel discharge information and correlated X-Y or X-Y-Z events. Recording of X-Y or X-Y-Z positions and histogramming counting rates versus positional locations are implemented in one embodiment by field programmable gate array (FPGA) logic devices. FIG. 15 is a block diagram of readout electronics coupled to a PPS or PPPS cell matrix 282 in accordance with one embodiment. The readout electronics includes a discriminator 284 to condition the signals for FPGA processors 286. Since the PPS and PPPS signal integration is inherently digital, with an electron gain on the order of $10^6$ or greater for a cell pitch of 0.10 mm, A/D converters and/or amplification electronics are not required for most of the applications for which these detectors are designed. For lower resolution panels with a larger pitch, or for panels having a large effective cell capacitance, the electron gain will be greater than $10^6$. Also the duty cycle should be a few orders-of-magnitude less than for PDP video monitors which are AC devices with high capacitance, thus the DC type PPS and PPPS detectors described here have low capacitance will consequently have very low power consumption.

In a number of embodiments, the detector can operate synchronously in a clocked mode with timing intervals that can be less than a nanosecond. The cells of the detector can provide a single digital bit for each time interval. Timing at this rate is within the capability of a typical FPGA which is well suited and has the flexibility to examine the temporal and positional information in the bit streams. The speed of these embodiments also makes possible their use as trigger elements in an accelerator when adjacent layers are combined to define a trajectory compatible with particles of interest. This usually represents the selection of tracks of near normal incidence to the plane of the detector. Less interesting tracks are bent away from normal incidence by magnets.

Fast-Timing Readout Electronics

Embodiments disclosed herein may include readout electronics to determine the number of cells fired and the mean location of a "hit" within the detector. The electronics also measure the time between an "external" event and the discharge of a pixel or a close grouping of pixels. Individual pixel discharge rise times (e.g., 10% to 90%) for PPS and PPPS embodiments configured to have the minimum effective cell capacitance may be on the order of a few picoseconds at the low end, but could also be in the upper sub-nanosecond range depending upon the detector resolution, materials and device structure. However most "meaningful" discharge events generally consist of the superposition of many pixels firing, so the time resolution readout for that superposition of pulses is longer, but can still be better than 100 ps.

In a PPS or PPPS embodiment, an event can occur when a particle or photon entering the device creates ionization in the gas volume. The extremely high field generated across the discharge electrodes (i.e., X- and Y-electrodes), on the order of 10 MV/m, results in fast electron drift velocities across the small discharge gap thus producing the fast rise times associated with these devices. The huge multiplication effect in the gas, with a gain on the order of $10^6$, dramatically increases the size of the initial ionization signal. For the PPS/PPPS embodiments shown in FIGS. 1, 7-8, 11-14 and 16 there are three distinct sets of electrodes which combine to form a pixel site. They are the Y-electrode (anode), the X-electrode (cathode), and the orthogonal Z-electrode which is located beneath the X-Y electrode pair and isolated by either a thin dielectric substrate or a dielectric layer. When triggered by an ionization event in the gas, the high field associated with the X- and Y-electrodes generates a plasma avalanche in the shape of a surface-discharge with characteristics somewhat similar to the surface-discharge created at each pixel site in a PDP-TV. However, in the PPS and PPPS embodiments, the discharge is much faster primarily because of the much lower pixel capacitance of the discharge cell (a DC device), as compared to the PDP (an AC device), but also due to the higher field and different gas mixtures. The signals from all three electrodes thus generate position, pixel count and timing information.

A given pair of surface discharge X- and Y-electrodes is generally shared by many pixels. The output signal pulses will be an aggregate of the charge deposited by multiple discharge events in the pixels. Either anode or cathode signals can be used to generate a trigger for events in the PPS or PPPS embodiments. However the component of the signal which is generated by the movement of electrons to the Y-electrode/anode (sense) will typically be very fast, while the component of the signal that is generated by the movement of positive ions to the X-electrode/cathode (discharge electrode) will be slow. The total quantity of charge generated is due to electron multiplication, and the time to collect this charge on the anode/cathode pair will determine the duration of the pulse. With a single emitted free-electron experiencing a gain on the order of $10^6$, the fast component of the generated charge, the electrons, reaching the anode will thus generate a large current spike due to the very short rise time associated with this electron charge migration. The much longer fall time associated with the same pixel discharge is primarily due to the secondary current component arising from the slow ion drift to the cathode. As a general rule the ion drift component tends to be about two orders-of-magnitude slower than the electron drift. Thus a 10 ps rise time might be associated with a 1 ns fall time. The large current pulse per pixel discharge event associated with the high gain and short rise time, multiplied by the number of such events occurring within a period of perhaps a few nanoseconds in different pixels on a given electrode, will produce a correspondingly larger output pulse.

To collect tracking location/positional information of activated (i.e., discharging) pixels, each electrode in one embodiment includes a current-limiting impedance, typically a "quenching resistor", to prevent run-away discharges and to determine the location of each discharge event by measuring the electrode voltage drop. When a discharge occurs, it produces a rapid change in voltage on the X- and Y-electrodes. The sense of the change on the cathode will be the opposite to the sense of the change on the anode. The amplitude of the discharge (i.e., current) can be limited as necessary, either by adding a quenching agent to the gas or by the use of a series quenching impedance. To determine the precise pixel discharge location in two-dimensions, a third, orthogonal strip electrode can be fabricated either under the X- and Y-electrodes (i.e., electrically isolated by a dielectric insulator layer as shown in FIG. 14) or on the PPS or PPPS bottom substrate backside as shown in 1, 7-8, 11-13 and 16 (assuming that the bottom substrate is of a dielectric insulator material and no more than a few millimeters thick). This third electrode (i.e., Z-electrode), which runs orthogonal to the discharging X- and Y-electrodes, serves a function similar to the "back strip" electrodes in a Cathode Strip Detector or large area MicroStrip Gas Chamber (MSGC) detector, that is to fix the discharge position in the orthogonal direction. For a given discharge event, the rapid change in the associated discharge electrode voltage will be capacitively coupled into the Z-electrode producing a somewhat similar voltage pulse. The magnitude and shape of this pulse will be determined by the capacitance between the X- and Z-electrodes, the Y- and Z-electrodes, and the other impedances attached to the Z-electrode. Simple field calculations assuming that the dielectric is glass suggest that the induced signal could be 10% to 30% that of the anode. The output signal from the Z-electrode will thus be smaller than the output from the X- and Y-electrodes, but should still be significant and can therefore be used to obtain the positional location. In one embodiment, the Z-electrode in the above referenced cathode strip detector has a pulse height about one-quarter that of the Y-electrode (anode) and a position resolution of better than 100 µm. In terms of the Z-electrode circuit, a charge division network can be connected to a group of Z-electrodes to form a segment. In order to maximize the capacitive coupling between the X- and Z-electrode, in one embodiment the thickness of the dielectric which separates them is minimized, but not so much as to incur dielectric breakdown. Finally, instead of an external electrode line impedance as shown for the columnar-discharge embodiment of FIG. 2, an internal impedance element (e.g., resistor) can be patterned into each pixel to reduce the discharge dead-time and to allow each pixel to operate independently of other pixels on the same electrode line. The use of embedded pixel resistors as shown in FIGS. 1 and 11-14 also helps control avalanche spreading, and for a number of PPS and PPPS detector embodiments the use of embedded pixel resistors are all that is needed to achieve avalanche cell localization. Although not shown, various embodiments of FIGS. 7, 8 and 16 also include embedded pixel resistors similar to those in FIGS. 1 and 11-14.

The quantity of charge produced by a single discharge event in an embodiment having a gain of $10^6$ will be $1.6 \times 10^{-13}$ coulombs, and for a high resolution PPS or PPPS embodiment this charge could be generated and move across the discharge gap in a time period on the order of a nanosecond (or faster) thus corresponding to approximately 0.1 ma of current. The effect of multiple discharges (pixel hits) on a single electrode will produce a correspondingly larger output pulse, as will a higher effective pixel capacitance corresponding to a higher gain. The output from many Y-electrodes can be combined using a charge division network. The pulse signals generated by the charge division networks can be processed and used to estimate arrival time, energy, and location of the incident particle. The voltage pulse output from the Z-electrodes can also be combined using a charge division network. The Z-electrode output will be smaller but sufficient to estimate the second position coordinate of the incident particle.

Applications

In some embodiments, the combination of very high spatial resolution along with time-of-flight (TOF) capability in the range of 100 ps, coupled with insensitivity to magnetic fields and radiation hardness, has the potential to yield order-of-magnitude advances in a multitude of applications, such as detectors for radioactive ion beam (RIB) accelerators, beam monitors for RIB profile and target diagnostics, high energy neutron research including neutron calorimeters, focal plane tracking detectors, gamma-ray tracking detectors (e.g., Compton telescopes), minimum ionizing particle (MIP) detectors (e.g., muons, etc.) such as for the planned upgrade of the Large Hadron Collider (LHC) at CERN, neutron and gamma-ray detectors with high discrimination capability for active interrogation in homeland security, passive neutron and gamma-ray detectors for homeland security, improved hadron particle beam therapy for cancer/tumor irradiation (e.g., with protons, carbon ions and neon ions) via better accelerator beam control and real-time beam measurement using PPS Active Pixel Beam Monitors, numerous gamma-ray detectors for improved nuclear medicine imaging modalities including PET/CT, PET/MRI, SPECT, SPECT/MRI, multislice-CT, computed tomography angiography (CTA), scintillation mammography, bright-field and dark-field X-rays, etc. The various detector embodiments, structures, materials, configurations and circuitry shown in FIGS. 1-16 are directed towards addressing the above described applications.

Many of the PPS and PPPS embodiments have properties that make them particularly suitable for high energy and nuclear physics research. For example, both the PPS and PPPS devices offer extraordinary pixelation, allowing precise position measurements. They operate at very high gains in each pixel, so they can trigger under very low incident flux. The pixel discharge has a very rapid rise time and thus can provide an excellent timing detector. This combination of properties for example makes the PPPS an attractive candidate for a Cherenkov detector, as disclosed above and in the embodiment shown in FIG. 13. Further, most of the embodiments described are relatively inexpensive to manufacture for large areas. The projected costs for covering 1 m$^2$ with PPS devices manufactured in reasonable volumes can be comparable to the cost of a few 2-inch diameter photomultiplier tubes.

In embodiments concentrating on charged particle breakup reactions, better position resolution should permit embodiments to be placed closer to the target and cover more solid-angle, reducing the time needed for already difficult measurements. The PPPS embodiments in these applications would need to cover areas on the order of about 1 m$^2$. A time resolution of ~100 ps is definitely within the capability of the previously disclosed PPPS readout electronics. This time resolution capability is in addition to the same circuit being able to read out both the incident particle energy and its positional "hit" location (for each event) within the scintillator, the latter with sub-millimeter resolution (depending of course upon the choice of scintillator material and thickness). Achieving 100 ps time resolution also enables time-of-flight measurements that could help discriminate neutrons and other particles from photons for a variety of applications. Such capability is also enabling for time-of-flight temporal filtering and image enhancement for various medical imaging modalities, including applications such as time-of-flight PET/CT imaging systems.

Low-Energy Radioactive Ion Beam (RIB) Profile Diagnostics

Intensity profiles and emittance analyses are among the most critical tools used for optimizing beam transport through accelerators. Embodiments of the PPS are highly position and intensity sensitive (intensity via number of cells firing repeatedly). In detecting charged particles for RIB-profile diagnostics, the embodiments do not require any type of converter for the range of beam energies of prime interest for most low-energy studies. Charged particles passing through the active gas volume of the device will create free-electrons by collisions with the gas atoms. The probability of interaction at a given ion velocity increases significantly with atomic number, and so there would be a large amount of interaction at 100 MeV/nucleon for $^{124}$Sn or $^{238}$U. One problem at very low beam energies is getting the ion through the front substrate without losing a large amount of its energy. In order to accomplish this, one embodiment is a PPS with an ultra-thin foil front substrate, which if needed can be strengthened by means of an external wire matrix reinforcement grid. The basic design for such a PPS Active Pixel Beam Profile Monitor to be used for beam diagnostics at low energies is disclosed in FIG. 7.

Active Pixel Beam Monitors for Particle Beam Diagnostics

Embodiments can provide real-time diagnostics with very low intensity particle beams produced by radioactive ion beam (RIB) facilities. Embodiments can be used for beam imaging and counting detectors (i.e., beam position monitors) that can be dropped into the beam for a "destructive" measurement—that is, one in which the beam is stopped. By constructing a PPS embodiment using an extremely thin (e.g. ~3 μm) front substrate (e.g., sol-gel formed alumina, etched ceramics such as Si$_3$N$_4$, etched glass, metal foil or an ultra-thin superalloy foil), the PPS could be used for example at RIB energies as low as 1 MeV per nucleon for essentially any element. The exact substrate thickness can be estimated for the beams and energies to be used, but ultra-thin foils can be employed for most beams, especially in larger diameters, if supported by a proper external wire reinforcement matrix arrangement. In a low energy RIB accelerator, even a 25 μm substrate/window of plastic will stop the lower energy heavier ions, but a 3 to 6 μm thick, superalloy foil such as Arnavar™ provides an excellent window/substrate. More specifically, for the described application in one embodiment the PPS active area need only be about 1.0 to 1.5 cm in diameter. It thus follows that a 6 μm Arnavar™ foil window placed in tension by hermetically sealing it to a lower expansion, relatively thick (e.g., 3 mm) glass substrate, such as fused silica or a non-alkali borosilicate type glass, functions in a vacuum accelerator environment without significant physical distortion (i.e., "bowing out" of the foil due to the positive internal gas pressure in relation to the "outside" vacuum) and hence without the need for external wire reinforcement, as shown in FIG. 7. By purposely coupling (i.e., sealing) the above foil material to a much lower expansion coefficient "thick" back-plate substrate, the superalloy foil can be forced to be in a condition of "permanent" tension, thus giving it enhanced mechanical strength to resist further stretching caused by the positive internal gas pressure. Larger active area PPS embodiments, however, would likely require external wire reinforcement.

For the above described PPS beam monitor embodiment, in one embodiment the materials and fabrication processing would be as follows. FIG. 7 is a cross-sectional view of a PPS beam monitor in accordance with one embodiment. Arnavar™ foil (commercially available and tested with a thickness of 6 μm) having a linear expansion coefficient of 125×10$^{-7}$/° C. would be sealed to a "thick" borosilicate glass substrate (e.g., ~3 mm) having a linear expansion coefficient of 32×10$^{-7}$/° C. The Arnavar™ foil would thus be put in tension with respect to the lower expansion glass substrate after both materials are sealed at high temperature—i.e., as both materials cool the Arnavar™ foil wants to contract faster than the borosilicate glass but is restrained from doing so by the strength of the glass seal. For small area devices at about a half atmosphere of internal pressure (e.g., up to ~1.5 cm in diagonal), the Arnavar™ foil will resist distortion when placed in an external vacuum environment. For maximum seal strength, a crystallizing solder-glass frit seal should be employed. If more tension is needed for the Arnavar™ foil, then instead of a borosilicate substrate, a lower expansion and high temperature sealing substrate can be used such as fused silica which has an expansion coefficient of $6 \times 10^{-7}/°$ C.

Focal Plane Detectors at Intermediate Energies

At intermediate energies, the PPS embodiments can be used as a very high-resolution, fast position detector for many applications. At accelerators such as the National Superconducting Cyclotron Laboratory (NSCL), fast beams are often characterized by "tracking", i.e. by determining their positions at various points before and after reactions. The detectors used in these applications typically range from 10 cm$^2$ in the beam analysis lines, to 0.25 m$^2$ in the focal plane of magnetic spectrometers. This tracking is currently done with relatively slow, fragile gas discharge detectors with gas pressures of about 140 torr. These have position resolutions on the order of 1 mm or less, but are restricted to low count rates by the slow charge collection time in larger detectors. A PPS embodiment made with thin entrance and exit windows could replace these fragile detectors with a more robust and much faster detector with comparable or better position resolution. Ultra-thin front substrate alternatives exist for viable PPS devices such as 3 to 6 µm Arnavar™ foil, as well as an ultra-thin "fused" sapphire type material that might also be available in a thickness of ~3 µm. All these detectors operate in vacuum and therefore depending upon the PPS internal gas pressure and internal spacer bonding technology, might very well require some form of external wire reinforcement or support structure. Embodiments such as that shown in FIG. 16 should be able to transmit the particles with only a few percent energy-loss. To meet this requirement, embodiments should be constructed using an ultra-thin metal foil or ceramic front substrate (window) as described above. For example, a 100 MeV/nucleon $^{132}$Sn ion loses less than 1% of its energy in traversing a 6 µm titanium-foil, and less than 2% of its total energy traversing a detector made with this Ti-foil window, with Xe gas at 140 torr, and a 50 µm glass substrate for the surface-discharge electrodes.

Active Pixel Beam Detectors for Hadron Beam Therapy

The ultra-thin, low mass, PPS detectors embodiments, as shown for example in FIGS. 7 and 16, also have the requisite characteristics needed for the next generation of particle detectors for cancer treatment by hadron beam therapy of tumors. In particular, the proton, carbon and neon ion beams presently being used on these tumors require active pixel detection without significantly altering the incident beam energy, intensity, direction, focus or collimation, and most importantly without introducing significant particle/photon scattering to the patient.

Other Embodiments

For many applications, a particular ionizing radiation detector system could benefit significantly by a vertical stacking of the PPS and/or PPPS detector embodiments described herein, and such detector arrangements and configurations would be obvious to anyone skilled in the art of designing such detection systems. As one example, the vertical stacking of PPPS Cherenkov detectors and/or PPS particle detectors, or combinations of such PPPS and PPS detectors (e.g., embodiments shown in FIGS. 1, 7, 11-14), would provide significantly enhanced particle trajectory tracking and timing (e.g., time-of-flight) information as well as providing a means to filter or separate MIP induced discharges from a Cherenkov photon signal.

A number of embodiments are specifically illustrated and/or described herein. However, it will be appreciated that modifications and variations of the disclosed embodiments are covered by the above teachings and within the purview of the appended claims without departing from the spirit and intended scope of the invention.

What is claimed is:

1. A position-sensitive ionizing-particle radiation counting detector comprising:
   a first substrate;
   a second substrate generally parallel to said first substrate and forming a gap with said first substrate;
   a discharge gas contained within said gap;
   at least one first electrode electrically coupled to said second substrate;
   at least one second electrode electrically coupled to the first electrode and defining at least one pixel with the first electrode, wherein the first electrode and the second electrode are in direct contact with the discharge gas;
   a patterned dielectric barrier structure, forming a plurality of cells, layered over and directly coupled, without an intervening dielectric layer, to at least one of said first or second electrodes, the patterned dielectric barrier structure directly coupled to both the first and the second substrates, and in direct contact with the discharge gas;
   a current-limiting quench resistor coupled in series to at least one of said first or second electrodes;
   a power supply coupled to at least one of the first or second electrodes;
   a first discharge event detector circuitry coupled to at least one of the first or second electrodes for detecting a gas discharge counting event in the electrode;
   a plurality of pixels defined by said electrodes, each pixel capable of outputting a gas discharge counting event upon interaction with ionizing-particles, wherein each gas discharge pulse is counted as having approximately an equal value; and
   circuitry for detecting if a gas discharge counting event pulse is output from the pixels, and for counting each gas discharge pulse as an individual event;
   wherein the dielectric barrier structure is configured to localize each gas discharge counting event to one of the plurality of cells.

2. The radiation counting detector of claim 1, wherein an amount of detected ionizing-particle radiation is based on a total count of individual events.

3. The radiation counting detector of claim 1, further comprising a hermetic seal coupled to said first and second substrates.

4. The radiation counting detector of claim 1, wherein said power supply is a direct current (DC) power supply.

5. The radiation counting detector of claim 1, wherein a gas discharge between the first and second electrodes is a surface-discharge shape.

6. The radiation counting detector of claim 1, wherein a gas discharge between the first and second electrodes is a columnar-discharge shape.

7. The radiation counting detector of claim 1, wherein said dielectric barrier structure comprises a matrix of vertical wall barriers.

8. The radiation counting detector of claim 1, wherein at least one of said substrates is an ultra-thin substrate.

9. The radiation counting detector of claim 1, further comprising at least one current-limiting quench resistor coupled in series with each of said pixels.

10. A position-sensitive ionizing-particle radiation counting detector comprising:
   a first substrate;
   a second substrate generally parallel to said first substrate and forming a gap with said first substrate;
   a discharge gas contained within said gap;
   at least one first electrode electrically coupled to said second substrate;
   at least one second electrode electrically coupled to said first electrode and defining at least one pixel with said first electrode, wherein said first electrode is a Y-electrode and said second electrode is an X-electrode, wherein the first electrode and the second electrode are in direct contact with the discharge gas;
   a patterned dielectric barrier structure, forming a plurality of cells, layered over and directly coupled, without an intervening dielectric layer, to at least one of said X- or Y-electrodes, the patterned dielectric barrier structure directly coupled to both the first and the second substrates, and in direct contact with the discharge gas;
   a current-limiting quench resistor coupled in series to at least one of said X- or Y-electrodes;
   a direct current power supply coupled to at least one of said X- or Y-electrodes;
   a first discharge event detector circuitry coupled to at least one of said X- or Y-electrodes for detecting a gas discharge counting event in said electrode;
   a plurality of pixels defined by said electrodes, each pixel capable of outputting a gas discharge counting event pulse upon interaction with ionizing-particles, wherein each gas discharge pulse is counted as having an approximately equal value; and
   circuitry for detecting if a gas discharge counting event pulse is output from the pixels, and for counting each gas discharge pulse as an individual event;
   wherein the dielectric barrier structure is configured to localize each gas discharge counting event to one of the plurality of cells.

11. The radiation counting detector of claim 10, wherein an amount of detected ionizing-particle radiation is based on a total count of individual events.

12. The radiation counting detector of claim 10, further comprising a hermetic seal coupled to said first and second substrates.

13. The radiation counting detector of claim 10, wherein said dielectric barrier structure comprises a matrix of vertical wall barriers.

14. The radiation counting detector of claim 10, wherein a gas discharge between said X- and Y-electrodes is a surface-discharge shape.

15. The radiation counting detector of claim 10, wherein a gas discharge between said X- and Y-electrodes is a columnar-discharge shape.

16. The radiation counting detector of claim 10, wherein at least one of said substrates is an ultra-thin substrate.

17. The radiation counting detector of claim 10, further comprising at least one current-limiting quench resistor coupled in series with each of said pixels.

18. A position-sensitive ionizing-particle radiation counting detector comprising:
   a first substrate;
   a second substrate generally parallel to said first substrate and forming a gap with said first substrate;
   a discharge gas contained within said gap;
   at least one first electrode electrically coupled to said second substrate;
   at least one second electrode electrically coupled to said first electrode and defining at least one pixel with said first electrode, wherein said first electrode is a Y-electrode and said second electrode is an X-electrode, wherein the first electrode and the second electrode are in direct contact with the discharge gas;
   a patterned dielectric barrier structure, forming a plurality of cells, layered over and directly coupled, without an intervening dielectric layer, to at least one of said X- or Y-electrodes, the patterned dielectric barrier structure directly coupled to both the first and the second substrates, and in direct contact with the discharge gas;
   a current-limiting quench resistor coupled in series to at least one of said X- or Y-electrodes;
   a direct current power supply coupled to at least one of said X- or Y-electrodes;
   a first discharge event detector circuitry coupled to at least one of said X- or Y-electrodes for detecting a gas discharge counting event in said electrode, wherein said gas discharge between said X- and Y-electrodes is a surface-discharge shape;
   a plurality of pixels defined by said electrodes, each pixel capable of outputting a gas discharge counting event pulse upon interaction with ionizing-particles, wherein each gas discharge pulse is counted as having an approximately equal value; and
   circuitry for detecting if a gas discharge counting event pulse is output from the pixels, and for counting each gas discharge pulse as an individual event;
   wherein the dielectric barrier structure is configured to localize each gas discharge counting event to one of the plurality of cells.

19. The radiation counting detector of claim 18, further comprising at least one current-limiting quench resistor coupled in series with each of said pixels.

20. The detector of claim 18, further comprising a third electrode coupled to said first substrate.

21. The detector of claim 20, wherein said first substrate is an ultra-thin substrate.

22. The detector of claim 18, wherein said first substrate is an ultra-thin substrate.

23. The detector of claim 18, wherein said first and second substrates are ultra-thin substrates.

24. A position-sensitive ionizing-particle radiation counting detector comprising:
   a first substrate;
   a second substrate generally parallel to said first substrate and forming a gap with said first substrate;
   a discharge gas contained within said gap;
   at least one first electrode electrically coupled to said second substrate;
   at least one second electrode electrically coupled to said first electrode and defining at least one pixel with said first electrode, wherein said first electrode is a Y-electrode and said second electrode is an X-electrode, wherein the first electrode and the second electrode are in direct contact with the discharge gas;
   an open dielectric structure pattern, forming a plurality of cells, layered over and directly coupled, without an intervening dielectric layer, to at least one of said X- or Y-electrodes, the patterned dielectric barrier structure directly coupled to at least one of said first or second substrates, and in direct contact with the discharge gas;

a current-limiting quench resistor coupled in series to at least one of said X- or Y-electrodes;

a direct current power supply coupled to at least one of said X- or Y-electrodes;

a first discharge event detector circuitry coupled to at least one of said X- or Y-electrodes for detecting a gas discharge counting event in said electrode, wherein said gas discharge between said X- and Y-electrodes is a columnar-discharge shape;

a plurality of pixels defined by said electrodes, each pixel capable of outputting a gas discharge counting event pulse upon interaction with ionizing-particles, wherein each gas discharge pulse is counted as having an approximately equal value; and circuitry for detecting if a gas discharge counting event pulse is output from the pixels, and for counting each gas discharge pulse as an individual event;

wherein the dielectric structure pattern is configured to localize each gas discharge counting event to one of the plurality of cells.

25. The radiation counting detector of claim 24, further comprising at least one current-limiting quench resistor coupled in series with each of said pixels.

26. The detector of claim 24, wherein said first substrate is an ultra-thin substrate.

27. The detector of claim 24, wherein said first and second substrates are ultra-thin substrates.

28. A method of detecting ionizing-particle radiation based on a counting of gas discharge events within a discharge gas, the method comprising:

receiving ionizing-particle radiation at a first substrate coupled to a second substrate with at least one first electrode electrically coupled to said second substrate and at least one second electrode electrically coupled to said first electrode, wherein a patterned dielectric barrier structure, forming a plurality of cells, is layered over and directly coupled, without an intervening dielectric layer, to at least one of said first or second electrodes, the patterned dielectric barrier structure directly coupled to at least one of said first or second substrates, and is in direct contact with the discharge gas, and at least one pixel is defined with said first electrode, wherein the first electrode and the second electrode are in direct contact with the discharge gas;

creating at least one ion-pair in the discharge gas contained within a gas gap between the first and second substrates;

causing a gas-discharge event at a pixel site, wherein the discharge event is isolated by the dielectric barrier structure; and counting a plurality of the events at a pulse detector coupled to either said first or second electrodes, wherein each of the events is counted as approximately an equal value;

wherein the dielectric barrier structure is configured to localize each gas discharge counting event to one of the plurality of cells.

* * * * *